US008481077B2

(12) United States Patent
Kheir et al.

(10) Patent No.: US 8,481,077 B2
(45) Date of Patent: Jul. 9, 2013

(54) MICROBUBBLES AND METHODS FOR OXYGEN DELIVERY

(75) Inventors: John Kheir, Brighton, MA (US); Mark Andrew Borden, New York, NY (US); Francis X. McGowan, Wellesley Hills, MA (US)

(73) Assignees: The Trustees of Columbia University in the City of New York, New York, NY (US); Children's Medical Center Corporation, Boston, MA (US)

( * ) Notice: Subject to any disclaimer, the term of this patent is extended or adjusted under 35 U.S.C. 154(b) by 0 days.

(21) Appl. No.: 13/402,409

(22) Filed: Feb. 22, 2012

(65) Prior Publication Data

US 2012/0156300 A1 Jun. 21, 2012

Related U.S. Application Data

(62) Division of application No. 12/240,704, filed on Sep. 29, 2008, now abandoned.

(60) Provisional application No. 61/073,334, filed on Jun. 17, 2008, provisional application No. 61/026,984, filed on Feb. 7, 2008, provisional application No. 60/975,705, filed on Sep. 27, 2007.

(51) Int. Cl.
*A61K 9/48* (2006.01)

(52) U.S. Cl.
USPC .......................................... 424/451; 424/489

(58) Field of Classification Search
None
See application file for complete search history.

(56) References Cited

U.S. PATENT DOCUMENTS

| 3,526,481 A | 9/1970 | Rubricius et al. |
| 4,446,642 A | 5/1984 | Chap |
| 4,466,442 A | 8/1984 | Hilman |
| 4,911,689 A | 3/1990 | Nattier |
| 5,084,011 A | 1/1992 | Grady |
| 5,219,538 A | 6/1993 | Henderson |
| 5,558,094 A | 9/1996 | Quay |
| 5,573,751 A | 11/1996 | Quay |
| 5,665,383 A | 9/1997 | Grinstaff |
| 5,711,933 A | 1/1998 | Bichon |
| 5,840,275 A | 11/1998 | Bichon |
| 5,863,520 A | 1/1999 | Bichon |
| 5,869,538 A | 2/1999 | VanLiew |
| 5,935,553 A | 8/1999 | Unger |
| 6,200,548 B1 | 3/2001 | Bichon |
| 6,416,740 B1 | 7/2002 | Unger |
| 6,443,898 B1 | 9/2002 | Unger |
| 6,808,720 B2 | 10/2004 | Unger |
| 6,844,317 B2 | 1/2005 | Winslow |
| 7,105,151 B2 | 9/2006 | Unger |
| 7,122,027 B2 | 10/2006 | Trescony |
| 7,303,156 B1 | 12/2007 | Kim |
| 2003/0120204 A1 | 6/2003 | Unger et al. |
| 2004/0013662 A1 | 1/2004 | Porter et al. |
| 2005/0260189 A1 | 11/2005 | Klibanov |
| 2010/0069814 A1 | 3/2010 | Borgia et al. |

FOREIGN PATENT DOCUMENTS

| EP | 0077752 | 4/1983 |
| EP | 0 605 477 B2 | 6/2007 |
| WO | 9516467 | 6/1995 |
| WO | 9700638 | 1/1997 |
| WO | 9818501 | 5/1998 |
| WO | WO 2004069284 | * 8/2004 |

OTHER PUBLICATIONS

Adjei and Garren, "Pulmonary delivery of peptide drugs: effect of particle size on bioavailability of leuprolide acetate in healthy male volunteers", Pharm. Res., 7:565-69 (1990).
Binshtok, et al., "Inhibition of nociceptors by TRPV1-mediated entry of impermeant sodium channel blockers", Nature, 449:607-610 (2007).
Choi and Maibach, "Liposomes and niosomes as topical drug delivery systems", J. Pharmacol and Biophys. Res.,18(5):209-19 (2005).
Cortesi, et al., "Sugar cross-linked gelatin for controlled release: microspheres and disks", Biomaterials 19:1641-1649 (1998).
Fozzard, et al., "Mechanism of local anesthetic drug action on voltage-gated sodium channels", Curr. Pharm. Des., 11:2671-2686 (2005).
Kohane, et al., "A re-examination of tetrodotoxin for prolonged duration local anesthesia", Anesthesiology, 89:119-31 (1998A).
Kohane, et al., "Sciatic nerve blockade in infant, adolescent, and adult rats: a comparison of ropivacaine with bupivacaine", Anesthesiology, 89:1199-1208 (1998B).
Masters, et al., "Prolonged regional nerve blockade by controlled release of local anesthetic from a biodegradable polymer matrix", Anesthesiology, 79 (2):340-346 (1993).
McLure and Rubin , "Review of local anaesthetic agents", Minerva Anesthesiol., 71:59-74 (2005).
Padrea, et al., "Tetrodotoxin for prolonged local anesthesia with minimal myotoxicity", Muscle Nerve, 34:747-53 (2006).
Ruetsch., et al., "From cocaine to ropivacaine: the history of local anesthetic drugs", Curr. Top. Med. Chem., 1:175-182 (2001).

(Continued)

*Primary Examiner* — Brian Gulledge
*Assistant Examiner* — Snigdha Maewall
(74) *Attorney, Agent, or Firm* — Wolf, Greenfield & Sacks, P.C.

(57) ABSTRACT

Compositions containing a carrier and microbubbles encapsulating one or more gases, preferably oxygen, and methods for making and using the compositions are described herein. The microbubbles contain a lipid envelope. The compositions may be administered to a patient to quickly deliver large amounts of oxygen to the patient's blood supply or directly to a tissue in need of oxygen. The compositions may be administered via injection or as a continuous infusion. The compositions contain a concentrated microbubble suspension, where the suspension contains at least 40 mL oxygen/dL suspension. The microbubbles are preferably less than 20 microns in diameter, more preferably less than 15 microns in diameter. The microbubbles described herein may be administered to a patient in an effective amount to increase in oxygen concentration in the patient's blood, and/or one or more tissues or organs.

14 Claims, 7 Drawing Sheets

OTHER PUBLICATIONS

Scholz, "Mechanisms of (local) anaesthetics on voltage-gated sodium and other ion channels", Br J. Anaesth., 89:52-61 (2002).

Zanen, et al., "The optimal particle size for parasympathicolytic aerosols in mild asthmatics", J. Int. J. Pharm., 114: 111-115 (1995).
Akerman, et al., "Penetration enhancers and other factors governing percutaneous local anaesthesia with lidocaine", Acta Pharmacol. Toxicol.,45 (1):58-65 (1979).
Bucana, et al., "Preservation of multilamellar lipid vesicles (liposomes) for ultrastructural studies", Scan Electron Microsc, (Pt 3):1329-37 (1983).
Burkhard, et al, "Oxygen transport to tissue by persistent bubbles: theory and simulations", J. Appl. Physiol., 77(6):2874-8 (1994).
Cabrales, et al., "Early difference in tissue pH and microvascular hemodynamics in hemorrhagic shock resuscitation using polyethylene glycol-albumin- and hydroxyethyl starch-based plasma expanders", Shock 24(1):66-73 (2005).
Cabrales, et al., "Extreme hemodilution with PEG-hemoglobin vs. PEG-albumin", Am J Physiol Heart Circ Physiol, 289(6):H2392-400 (2005).
Choi, et al., "Noninvasive, transcranial and localized opening of the blood-brain barrier using focused ultrasound in mice". Ultrasound in Medicine and Biology, 33 (1):95-104 (2007).
Dewall, et al., "A simple, expendable, artificial oxygenator for open heart surgery", Surg. Clin. North Am., 1025-34 (1956).
Diebel, et al., "Right ventricular response after myocardial contusion and hemorrhagic shock", Surgery, 14(4):788-92; discussion 93 (1993).
Dressaire, et al., "Interfacial polygonal nanopatterning of stable microbubbles", Science, 320(5880):1198-20I (2008).
Dubourg, et al., "Failure of the loop diuretic torasemide to improve renal function of hypoxemic vasomotor nephropathy in the newborn rabbit", Pediatr Res, 47(4 Pt 1):504-8 (2000).
Duncan and Needham, "Test of the Epstein-Plesset model for gas microparticle dissolution in aqueous media: effect of surface tension and gas undersaturation in solution", Langmuir, 20(7):2567-78 (2004).
Elberger and Honig, "Double-labeling of tissue containing the carbocyanine dye DiI for immunocytochemistry", J Histochem Cytochem, 38(5):735-9 (1990).
El-Desoky, et al., "Effect of graded hypoxia on hepatic tissue oxygenation measured by near infrared spectroscopy", J Hepatol, 31(1):71-6 (1999).
Epstein and Plesset, "On the stability of gas bubbles in liquid-gas solutions", J. Chem. Physics, 18(11):1505-09 (1950).
Farook, et al., "Microbubbling by co-axial electrohydrodynamic atomization", Medical & Biological Engineering & Computing, 45(8):781-789 (2007).
Farook, et al., "Preparation of microbubble suspensions by co-axial electrohydrodynamic atomization", Medical Engineering & Physics, 29(7):749-754 (2007).
Feinstein, "The powerful microbubble: from bench to bedside, from introvascular indicator to therapeutic delivery system, and beyond", American. Journal of Physiology-Heart and Circulatory Physiology, 287(2):H450-H457 (2004).
Feinstein, et al., "Microbubble dynamics visualized in the intact capillary circulation", J. Am. Coll. Cardiol., 4(3):595-600 (1984).
Ferrara, et al., "Ultrasound microbubble contrast agents: fundamentals and application to drug and gene delivery", Annual Rev. Biomed. Eng., 9:415-447 (2007).
Fuchs, et al., "Ischemic hepatitis: clinical and laboratory observations of 34 patients", J Clin Gastroenterol, 26(3):183-6 (1998).
Gerber, et al., "Long lived microbubbles for oxygen delivery", Artif. Cells Blood Substit. Immobil. Biotechnol., 35(I):119-24 (2007).
Hansel, et al., "Metabolic syndrome is associated with elevated oxidative stress and dysfunctional dense high-density lipoprotein particles displaying impaired antioxidative activity", J Clin Endocrinol Metab, 89(10):4963-71 (2004).
Hattler, et al., "A respiratory gas exchange catheter: in vitro and in vivo tests in large animals", J. Thorac. Cardiovasc. Surg., 124(3):520-30 (2002).
Hernot and Klibanov, "Microbubbles in ultrasound-triggered drug and gene delivery", Advanced Drug Delivery Reviews, 60(10):1153-1166, (2008).
Jones, et al., "Demonstration of nonperfused myocardium in late hemorrhagic shock", Circ Shock, 5(2):97 104 (1978).
Karlsson, et al., "Dynamics of hepatic enzyme activity following birth asphyxia", Acta Paediatr, 95(11):1405-11 (2006).
Kheir, et al., "Novel oxygen-bearing nanoparticles provide dose-dependent oxygen delivery", Critic. Care Medic., 35(12):A16-16 (2007).
Kim and Franses, "New protocols for preparing dipalmitoylohosphatidylcholine dispersions and controlling surface tension and competitive adsorption with albumin at the air/aqueous interface", Colloids and Surfaces B-Biointerfaces, 43(3-4):256-266 (2005).
Kim and Greenburg, "Artificial oxygen carriers as red blood cell substitutes: a selected review and current status", Artif. Organs, 28(9):813-28 (2004).
Kim, "Mechanical properties, microstructure, and specific adhesion of phospholipid monolayer-coated microbubbles", Ph.D. Dissertation, Duke University, (1999).
Kim, et al., "Mechanical properties and microstructure of polycrystalline phospholipid monolayer shells: novel solid microparticles", Langmuir, 19 (20):8455-66 (2003).
Klemcke, et al., "Is survival time after hemorrhage a heritable, quantitative trait?: an initial assessment", Shock 29(6):748-53 (2008).
Klibanov, et al., "Amphipathic polyethyleneglycols effectively prolong the circulation time of liposomes", Febs Letters, 268(1):235-7 (1990).
Klibanov, et al., "Ultrasound contrast agents: development of the field and current status", Topics in Current Chemistry, 222:1-34 (2002).
Kuhl, et al., "Modulation of interaction forces between bilayers exposing short-chained chained ethylene-oxide headgroups", Biophysical Journal, 66(5):I479-88 (1994).
Kvale, et al., "Size fractionation of gas-filled microspheres by flotation", Separations Technology, 6(4):219-226 (1996).
Laine, et al., "Polyethylene glycol nephrotoxicity secondary to prolonged high-dose intravenous lorazepam", Ann Pharmacother, 29(11):1110-4 (1995).
Ledingham, "Heart failure in experimental refractory shock". Eur J Intensive Care Med, 2(3):111-7 (1976).
Leonov, et al., "Extending the golden hour of hemorrhagic shock tolerance with oxygen plus hypothermia in awake rats. An exploratory study", Resuscitation, 52 (2):193-202 (2002).
Li and Fogler, "Acoustic emulsification 1. instability of oil-water interface to form initial droplets", Journal of Fluid Mechanics, 88(Oct):499-7 (1978).
Li and Fogler, "Acoustic Emulsification 2, breakup of large primary oil droplets in a water medium", Journal of Fluid Mechanics, 88(0ct):513-7 (1978).
Lindner, "Microbubbles in medical imaging: current applications and future directions", Nature Rev. Drug Discovery, 3(6):527-532 (2004).
Lum, et al., "Ultrasound radiation force enables targeted deposition of model drug carriers loaded on microbubbles", Journal of Controlled Release, 111 (1-2):128-134 (2006).
Lundgren, et al., "Intravascular fluorocarbon-stabilized microbubbles protect against fatal anemia in rats", Informa Healthcare, 34:473-486 (2006).
Meade, et al., "Ventilation strategy using low tidal volumes, recruitment maneuvers, and high positive end expiratory pressure for acute lung injury and acute respiratory distress syndrome: a randomized controlled trial." JAMA, 299(6):637-45 (2008).
Mezzetti et al., "Oxidative stress and cardiovascular complications in diabetes: isoprostanes as new markers on an old paradigm", Cardiovasc Res, 47(3):475-88 (2000).
Mulholland, et al., "Investigation and quantification of the blood trauma caused by the combined dynamic forces experienced during cardiopulmonary bypass", Perfusion, 5(6):485-94 (2000).
O'Neill, et al., Acute myocardial infarction with hyperoxemic therapy (AMIHOT): a prospective, randomized trial of intracoronary hyperoxemic reperfusion after percutaneous coronary intervention, J. Am. Coll. Cardiol. 50(5):397-405 (2007).

Pancholl, et al., "Novel methods for preparing phospholipid coated microbubbles", European Biophysics Journal with Biophysics Letters, 37 (4):515-520 (2008).

Pu, et al., "Collapse and shedding transitions in binary lipid monolayers coating microbubbles", Langmuir, 22(7):2993-9 (2006).

Pu, et al., "Effect of microstructure on molecular oxygen permeation through condensed phospholipid monolayers", J. Am. Chem. Soc., 127(18):6524-5 (2005).

Sakai, et al., "Hemoglobin-vesicles as oxygen carriers: influence on phagocytic activity and histopathological changes in reticuloendothelial system", Am. J. Pathol., 159(3):1079-88 (2001).

Schubert, et al., "Using microbubbles to oxygenate blood: possible?", Engineering in Medicine and Biology Society, 2003. Proceedings of the 25th Annual International Conference of the IEEE, 1(17-21):431 34 (2003).

Stieger, et al., "Enhancement of vascular permeability with low-frequency contrast-enhanced ultrasound in the chorioallantoic membrane model", Radiology, 243(1):112-121 (2007).

Takalkar, et al., "Binding and detachment dynamics of microbubbles targeted to P-selection under controlled shear flow", Journal of Controlled Release, 96 (3):473-482 (2004).

Takasu, et al., "Effects of increased oxygen breathing in a volume controlled hemorrhagic shock outcome model in rats", Resuscitation, 45(3)209-20 (2000).

Talu, et al., "Long-term stability by lipid coating monodisperse microbubbles formed by a flow-focusing device", Langmuir, 22(23):9487-9490 (2006).

Talu, et al., "Maintaining monodispersity in a microbubble population formed by flow-focusing", Langmuir, 24:1745-1749 (2008).

Talu, et al., "Lipid-stabilized monodispersed microbubbles produced by flow focusing for use as ultrasound contrast agents", Ultrasonics Symposium, 2006 IEEE, 2-6:1568-1571 (2006).

Talu, et al., "Tailoring the size distribution of ultrasound contrast agents: possible method for improving sensitivity in molecular imaging", Molecular Imaging, 6(6): 384-392 (2007).

Tayar, et al., "Severe hyperosmolar metabolic acidosis due to a large dose of intravenous lorazepam", N Engl J Med, 346(16):1253-4 (2002).

Taylor, "Ostwald ripening in emulsions", Advances in Colloid and Interface Science, 75(2):107-163 (1998).

Tracy and Walia, "A method to fix lipids for staining fat embolism in paraffin sections", Histopathology, 41(1):75-9 (2002).

Unger, et al. "Therapeutic applications of lipid-coated microbubbles", Adv. Drug Deliv. Rev., 56(9):1291-314(2004).

Wheatley, et al., "Surfactant-stabilized contrast agent on the nanoscale for diagnostic ultrasound imaging", Ultrasound in Medicine and Biology, 32(1):83-93 (2006).

Winslow, et al., "Comparison of PEG-modified albumin and hemoglobin in extreme hemodilution in the rat", J Appl Physiol, 97(4):1527-34 (2004).

Wu and Nyborg, "Ultrasound, cavitation bubbles and their interaction with cells", Advanced Drug Delivery Reviews, 60(10):1103-1116 (2008).

Xu, et al., "Controllable gas-liquid phase flow patterns and monodisperse microbubbles in a microfluidic T junction device", Applied Physics Letters, 88(13) (2006).

Zhao, et al., "Radiation-force assisted targeting facilitates ultrasonic molecular imaging", Molecular Imaging 3 (3): 135-148 (2004).

[No Author Listed], Acute Myocardial Infarction with HyperOxemic Therapy II (AMIHOT II). Clinical Trials.gov. Last Accessed from http://clinicaltrials.gov/ct2/show/NCT00175058?tern=therox &rank=1 on Nov. 9, 2010. 5 pages.

[No Author Listed], DownStream System. Therox. Last Accessed from http://www.therox.com/products/downstream-system/index.cfm?print on Nov. 9, 2010. 1 page.

* cited by examiner

MICROBUBBLES AND METHODS FOR OXYGEN DELIVERY

CROSS-REFERENCE TO RELATED APPLICATIONS

This application is a divisional of pending prior application U.S. Ser. No. 12/240,704 filed Sep. 29, 2008, entitled "*Microbubbles and Methods for Oxygen Delivery*", by John Kheir, Mark Andrew Borden and Francis X. McGowan, which claims priority to U.S. Ser. No. 61/073,334, filed Jun. 17, 2008; U.S. Ser. No. 61/026,984, filed Feb. 7, 2008; and U.S. Ser. No. 60/975,705, filed Sep. 27, 2007.

The disclosures in the applications listed above are herein incorporated by reference.

FIELD OF THE INVENTION

This present invention relates to compositions and methods for gas perfusion of tissues, and especially delivery of an effective amount of oxygen to a patient to alleviate or prevent ischemic injury.

BACKGROUND OF THE INVENTION

Every human cell requires a constant supply of oxygen to maintain cellular structure and homeostasis. This supply is primarily provided by hemoglobin, which carries inspired oxygen from the pulmonary capillaries to the tissues. In cases where a patient's lungs are unable to transfer adequate amounts of oxygen to circulating erythrocytes, severe hypoxia results and can quickly lead to severe organ injury and death.

Restoration of blood oxygen tension is paramount to resuscitation of the majority of pathophysiologic states. Some clinical states, such as lung injury, airway obstruction, and intracardiac mixing, exhibit hypoxemia and desaturation refractory to medical efforts to restore levels of oxygen saturation sufficient to limit ischemic injury. Ischemic injury may take place within minutes or seconds of insufficient oxygen delivery. In these conditions, low oxygen tension can result in end-organ dysfunction, failure, and mortality. The ability to augment oxygenation quickly and non-invasively would have dramatic implications on the morbidity and mortality from acute hypoxia, in addition to a number of other clinical situations.

Conventional attempts to restore oxygen levels in patients utilize supportive therapy of the patient's respiratory system, most commonly by way of mechanical ventilation. However, patients with lung injury, comprising a significant population of intensive care unit patients, have difficulty exchanging oxygen across a damaged alveolar unit. This requires clinicians to increase ventilator pressures, often causing further lung injury and systemic inflammation. Significant morbidity and mortality has been associated with ventilator induced lung injury, and barotrauma to the lungs is often necessitated by inadequate systemic oxygen delivery. The ability to non-invasively supplement even small percentages of oxygen delivery may significantly reduce the morbidity of mechanical ventilation.

Furthermore, emergency efforts to deliver oxygen to a patient are often inadequate and/or require too long to take effect, either due to lack of an adequate airway or overwhelming lung injury. This results in irreversible injury to the brain and other organs. Initiation of rescue therapy in these patients is burdensome and time consuming, and is available only at a limited number of specialized health care centers. There remains a need to quickly deliver oxygen directly to the blood of patients, thereby preventing or minimizing irreversible injury due to hypoxemia.

Therefore it is an object of the invention to provide improved methods for delivering oxygen to patients, tissues or organs.

It is yet a further object of the invention to provide improved compositions for delivering oxygen to patients, tissues or organs.

It is a still further object of the invention to provide improved methods for producing compositions for delivering oxygen to patients, tissues or organs.

SUMMARY OF THE INVENTION

Compositions containing a carrier and microbubbles encapsulating one or more gases, preferably oxygen, and methods for making and using the compositions are described herein. The microbubbles contain a lipid envelope formed of at least one base lipid and at least one emulsifying agent. The compositions may be administered to a patient to quickly deliver large amounts of oxygen to the patient's blood supply or directly to a tissue in need of oxygen. The compositions may be administered via injection or as a continuous infusion. The compositions contain a concentrated microbubble suspension, where the suspension contains at least 40 mL oxygen/dL suspension. The microbubbles are preferably less than 20 microns in diameter, more preferably less than 15 microns in diameter. The microbubbles described herein may be administered to a patient in an effective amount to increase the oxygen concentration in the patient's blood, and/or one or more tissues or organs, preferably in an amount effective to prevent or alleviate ischemic injury. The microbubbles may be administered alone or in combination with other treatments as an adjective therapy.

DETAILED DESCRIPTION OF THE INVENTION

I. Compositions

Compositions containing a carrier and microbubbles encapsulating one or more gases, preferably where at least one gas is oxygen, for administration to patients, tissues or organs in need of treatment are described herein. The compositions are particularly preferred for quickly delivering large amounts of oxygen to a patient's blood supply or directly to a tissue or organ in need of oxygen. The compositions may be administered via injection or as a continuous infusion.

A. Microbubbles

Figure 1:
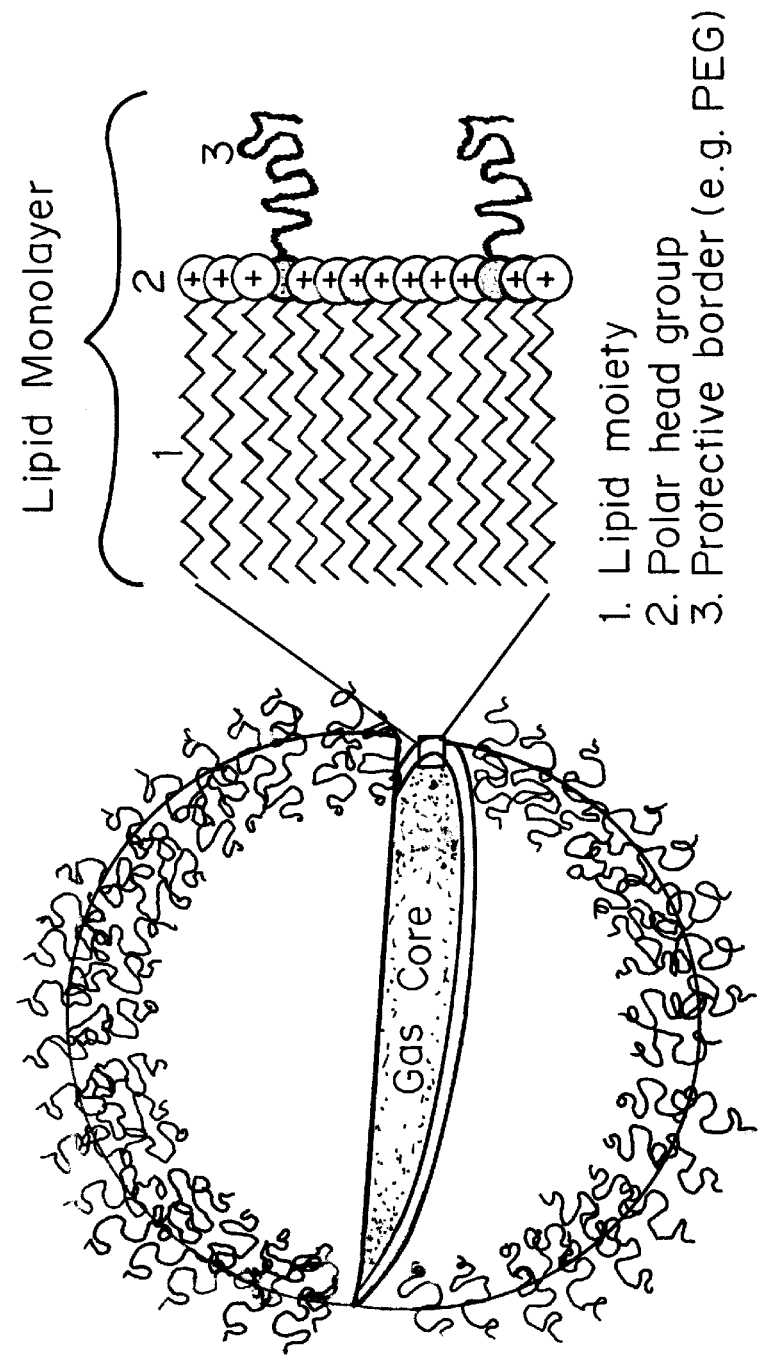
FIG. 1 is an illustration of a microbubble and its lipid envelope.

A typical structure for the microbubbles is illustrated in FIG. 1. As shown in FIG. 1, the microbubbles contain a gas core surrounded by an envelope formed from one or more lipids and one or more emulsifying agents in the form of a lipid monolayer or multilayer. The outer surface of the envelope forms a protective film, preferably formed from polyethylene glycol (see FIG. 1).

1. Envelope

The envelope is in the form of a lipid film, in the form of a monolayer or multilayer, preferably in the form of a monolayer. The lipid film may be between 1 and 100 nm thick, preferably between 1 and 10 nm thick, most preferably between 2 and 5 nm thick. In one preferred embodiment, the lipid film is a monolayer that is about 10 nm thick. A thin lipid film affords a high permeability to oxygen, while preventing a direct gas-blood interface.

Preferably the overall charge for the envelope is neutral.

The protective border prevents coalescence of the microbubbles through either a repulsive electrostatic double layer or a short-range repulsive steric barrier. The border also decreases recognition and uptake by the reticuloendothelial cells (RES) of the microbubble and inhibits complement activation and other immunogenic, toxic or thrombogenic effects. Typically, the envelope contains from 0.1 to 20% (molar), preferably from 5 to 10% (molar) emulsifying agent. The emulsifying agent generally contains a hydrophilic portion, typically a hydrophilic polymer, and a hydrophobic portion. The emulsifying agent or a portion thereof, generally the hydrophilic portion of the emulsifying agent, forms a protective border on the outer surface of the microbubble. Preferably the border is in the form of a brush where the hydrophilic portion of the emulsifying agent extends from the lipid containing portion of the envelope to form a border on the outer surface of the microbubble.

a. Lipids

A variety of lipids may be used to form the lipid film. The lipids may be natural or synthetic. Suitable lipids include phospholipids, fatty acids, triacyl glycerols, sphingolipids, terpenes, and waxes. Preferably the envelope contains one or more phospholipids.

Generally the lipid envelope contains at least one base lipid and at least one emulsifying agent, where at least a portion of the emulsifying agent forms a protective film on the outer surface of the envelope. "Base lipid" as used herein refers to the one or more lipids in the envelope that do not contain a component for forming a protective film that reduces surface tension, provides mechanical stability and limits gas diffusion.

The lipid envelope may contain lipids with acyl chains of varying lengths and degrees of saturation. The lipid envelope may contain lipids with a single acyl chain length, or different lipids with different acyl chain lengths. In a preferred embodiment, the lipid is a long-chain lipid, preferably a saturated diacyl phosphatidylcholine (Di-$C_n$—PC, where n is between 12 and 24, preferably where n is 16 or 18), which imparts low surface tension, high stability against envelope dissolution, and low gas permeability prior to administration in vivo. Suitable lipids include phosphocholines, phosphoglycerols, phosphatidic acids, phosphoethanolamines, and phosphoserines. Examples include 1,2-Dilauroyl-sn-Glycero-3-Phosphocholine (dilauroylphosphatidylcholine, DLPC), 1,2-Dimyristoyl-sn-Glycero-3-Phosphocholine (dimyristoylphosphatidylcholine, DMPC), 1,2-Dipentadecanoyl-sn-Glycero-3-Phosphocholine (dipentadecanoylphosphatidylcholine, DPDPC), 1,2-dipalmitoyl-sn-Glycero-3-Phosphocholine (dipalmitoylphosphatidylcholine, DPPC), 1-Myristoyl-2-Palmitoyl-sn-Glycero-3-Phosphocholine (1-myristoyl-2-palmitoylphosphatidylcholine, MPPC), 1,2-Dimyristoyl-sn-Glycero-3-[Phospho-rac-(1-glycerol)] (DMPG), 1,2-Dimyristoyl-3-Trimethylammonium-Propane, cholesterol and its derivatives, fatty acids, fatty alcohols, and fatty esters.

i. Acyl Chain Length

Lipids in the envelope may have different acyl chain lengths. The number of carbons in the acyl chains of the lipids may range from 10 to 24 carbons. The average acyl chain length of the lipids in microbubbles typically ranges from 10 to 24 carbons. For example, the average acyl chain length of the lipids may be 20, 18, 16, 14, 13, or 12 carbons. The envelope may include one or more synthetic lipids with asymmetric acyl chains, where one acyl chain is longer than another.

Lipids with longer acyl chain lengths are generally preferred compared to lipids with shorter chain lengths. Generally lipids with longer chain lengths produce more microbubbles with a greater shelf life. However, the chain length should not be too long, decreasing the rate of gas release in vivo.

Generally, longer chained lipids (e.g. 24-carbon vs. 16-carbon) are more resistant to oxygen passage. Resistance to gas release is also increased in walls composed of saturated (i.e. no double bonds) versus unsaturated lipids. Lipids with one or more double bonds contain kinks in the acyl chains due to the presence of the double bonds, which creates irregularities in the packing geometry, and thereby allows for gas to transfer out of the microbubble more rapidly.

Increasing or decreasing lipid acyl chain lengths in the microbubble may result in changes in the shearing properties of the envelope. Yield shear and surface viscosity may increase monotonically with hydrophobic chain length. A lipid film comprising lipids having longer chain lengths may have decreased permeability to gases compared to one with lipids with shorter acyl chain lengths. This decreased permeability may be attributed to an increase in attractive dispersion and hydrophobic forces between the hydrophobic tails of adjacent lipid molecules, resulting in a more cohesive lipid film. However, longer acyl chains generally provide greater envelope cohesion, which can improve mechanical strength and reduced gas escape kinetics.

Microbubbles containing lipids with longer acyl chain lengths may be stable in solution and exhibit prolonged persistence when mixed with desaturated blood.

In some applications for the microbubbles, microbubbles containing short acyl chain lengths (e.g. $\leq C14$) may be used for a rapid oxygen release profile. Shorter acyl chain lengths are generally more unstable than longer acyl chains. A microbubble with an envelope formed of lipids containing short acyl chains may require special mechanical or chemical processing to remain stable in suspension prior to injection into the bloodstream or mixing with another substance. Such special mechanical or chemical processing steps include cooling the suspension and creating of suspension just prior to injection.

ii. Phase Transition Temperature

As used herein, the "phase transition temperature" ($T_m$) refers to the temperature at which lipid assemblies transition from a solid (crystalline) phase to a fluid (liquid crystalline) phase. For example, 1,2-Dipentadecanolyl-sn-Glycero-3-Phosphoeholine (C15) has a $T_m$ of 33° C. Thus this lipid is in the solid phase at room temperature and transitions to the fluid phase when it is injected into the body.

Lipids in the fluid phase exhibit significantly higher thermal motion, creating a higher gas permeability and a significantly higher surface tension compared to the same lipids in the solid phase. Lipids in solid phase are tightly packed together with minimal lipid motion, making them less permeable to gas transfer. A microbubble containing lipids that are in the fluid phase generally has increased surface tension and gas permeability, which favors rapid dissolution of the microbubble, compared to the same microbubble containing the same lipids in the solid phase.

Shell cohesion, as a function of acyl chain length, may be represented by the reduced temperature ($T_R$), which is equal to the ratio of the ambient temperature (or "working temperature") (T) to the main phase transition temperature ($T_m$) of the lipid (in Kelvin). For $T_R>1$, the shell is in an expanded (fluid) state at the working temperature. For $T_R<1$, the shell is in a condensed (solid) state at the working temperature. See Table 2 for a list of lipids with their corresponding main phase transition temperatures ($T_m$) and reduced temperatures ($T_R$).

b. Emulsifying Agent

"Emulsifying agent(s)" refers to the one or more surfactants in the envelope that contain a molecule aiding lipid adsorption to the gas/liquid interface and stabilizing the microbubble to prevent coalescence. Typically, the surfactant is a hydrophilic polymer attached to a hydrophobic anchor via one or more covalent bonds. Preferably the hydrophobic anchor is a lipid. The hydrophobic anchor may be an alkyl group, in the form of a single chain or multiple chains. Typically the alkyl group is 12 to 24 carbons in length. Alternatively, hydrophobic anchors such as sterols, or polymers such as polycaprolactone may be used.

Preferably the hydrophilic polymer in the emulsifying agent is polyethylene glycol (PEG). Typical weight average molecular weights for PEG range from about 550 Da to 5,000 Da. Alternatively, other molecules can be in place of PEG. Alternatives include polypropylene glycol, polyvinyl alcohol, poly-N-vinyl pyrrolidone and copolymers thereof, mixed polyalkylene oxides having a solubility of at least one gram/liter in aqueous solutions such as some poloxamer nonionic surfactants, neutral water-soluble polysaccharides, including dextran, Ficoll, and derivatized celluloses, non-cationic poly (meth)acrylates, non-cationic polyacrylates, such as poly (meth)acrylic acid, and esters amide and hydroxyalkyl amides thereof, and combinations thereof.

The envelope may contain a variety of different amounts of base lipids and emulsifying agents. An optimum ratio of emulsifying agents to base lipids, which lies between a minimum ratio needed to have sufficient amounts of emulsifying agents to aid in lipid adsorption, shield the surface of the microbubble and prevent coalescence and a maximum ratio where lateral repulsion forces due to the presence of the emulsifying agent begin to significantly disrupt packing of the base lipid, may be determined experimentally.

Typically, the envelope contains from 0.1 to 20% (molar), preferably from 5 to 10% (molar) emulsifying agent. Suitable molar ratios of PEGylated lipids:base lipids include, for example, 1:99, 5:95, 10:90, 20:80, and 50:50. Preferably the ratio of PEGylated lipids:base lipids ranges from 5:95 to 10:90.

i. PEGylated Lipids

Emulsifying agents formed of a lipid and PEG are referred to herein as "PEGylated lipids".

In the preferred embodiment the emulsifying agent is a PEGylated lipid. The PEgylated lipid may contain the same lipid as the base lipid in the envelope. Alternatively, the PEGylated lipid may contain a lipid that is different from the base lipid in the envelope. Examples of suitable PEGylated lipids include 1,2-Distearoyl-sn-glycero-3-Phosphoethanolamine-N-[Methoxy(Polyethylene glycol)-1000], 1,2-Distearoyl-sn-glycero-3-Phosphoethanolamine-N-[Methoxy (Polyethylene glycol)-2000], and 1,2-Distearoyl-sn-glycero-3-Phosphoethanolamine-N-[Methoxy(Polyethylene glycol)-5000].

3. Optional Molecules

In one embodiment, one or more proteins or polymers may be used in place of the one or more lipids to stabilize the microbubble.

Optionally, the envelope may include one or more molecules in addition to the lipid(s) and emulsifying agent(s) to stabilize the microbubbles. Suitable stabilizers include polymers and proteins. Suitable polymers include lipophilic and amphiphilic polymers. The proteins and polymers may be within the lipid monolayer or multilayer.

The proteins may be a single protein or a mixture of proteins. Suitable proteins include lipophilic and amphiphilic proteins. Exemplary proteins include lung surfactant proteins, such as SP-A, SP-B, SP-C, or SP-D, synthetic lung surfactant proteins, lung surfactant protein mimetics, and derivatives thereof.

Alternatively the protein may be in a coating on the surface of the envelope.

2. Gas Core

The gas core contains at least one gas. The gas core does not contain a fluorinated gas. The gas must be pharmacologically acceptable, i.e. biocompatible and have minimal toxicity when released. Preferably the gas is able to diffuse through the envelope following administration. Preferably the gas is oxygen.

Other suitable gases include carbon dioxide, nitrogen, nitrous oxide, helium, argon, nitric oxide, xenon, carbon monoxide. These gases may be in the gas core alone or in combination with one or more other gases. For example, the gas core may contain a gas mixture containing oxygen and one or more additional gases.

In another embodiment, the gas contained within the microbubbles may be a biologically useful gas other than oxygen, including, but not limited to, nitric oxide, and volatile anesthetics, such as isoflurane.

B. Carrier

In one embodiment, the carrier is saline or another physiologically acceptable fluid. The carrier should be generally isotonic with blood. Suitable carriers include normal saline, physiological saline or water containing one or more dissolved solutes, such as salts or sugars, which do not substantially interfere with the formation and/or stability of the microbubbles.

In another embodiment, the carrier is a synthetic colloid, such as 6% hetastarch combined with a physiologically balanced crystalloid carrier that is similar to the plasma electrolyte balance (Hextend®, BioTime, Inc.), or hemoglobin-based oxygen carrier (HBOC), e.g. PolyHeme® (Northfield Laboratories, Evanston, Ill.), Hemopure® (HBOC-201) (Biopure Corp., Cambridge, Mass.), or HemoLink™ (Hb-raffimer) (Hemosol Inc, Toronto, Canada). In this embodiment, after the microbubbles release the oxygen in vivo, they leave behind the lipid envelope, which exhibits strong oncotic pressure, and carrier, which serves as a volume expander.

C. Excipients and Other Active Agents

In addition to containing the microbubbles, the carrier may contain excipients or other active agents.

The compositions should be generally isotonic with blood. Thus the compositions may also contain small amounts of one or more isotonic agents. The isotonic agents are physiological solutions commonly used in medicine and they comprise aqueous saline solution, e.g. 0.9% NaCl, 2.6% glycerol solution, lactated Ringer's solution, and 5% dextrose solution. The compositions may also be mixed with volume expanders, such as Hextend®, hetastarch, albumin, 6% Hydroxyethyl Starch in 0.9% Sodium Chloride Infusion (Voluven®), etc. The compositions can also be mixed with blood (e.g. packed red blood cells) or hemoglobin-based oxygen carriers. Additionally, the compositions can be mixed in a physiologic buffer (e.g. tris(hydroxymethyl)aminomethane, "THAM"). This is particularly useful in a clinical situation of impaired ventilation.

Active agents that can be included in the compositions include antioxidants and other factors known to mitigate injury.

D. Concentration of Microbubbles

The microbubbles are designed to release oxygen in clinically significant amounts quickly following injection, while minimizing build-up in the circulation of the components that form the envelope and carrier.

Thus, the injectable compositions generally contain high concentrations of microbubbles, in a minimal amount of carrier for the composition to be injected. Typical concentrations range from 70 to 90% (volume gas/volume injectable composition), preferably 80 to 90%. As shown in the Examples, suspensions containing from 40 to 70 mL oxygen per dL suspension have favorable mixing properties.

As shown in the Examples, the volume of the gas core is a function of the selection of the length of the acyl chains in the lipids that form the envelope. Further, the maximum packing density, which is a function of the microbubble size distribution and the shape and deformability of the microbubbles, limits the maximum gas fraction of the suspension. Preferably the volume of the gas core comprises 50% or more of the overall volume of the suspension. In one preferred embodiment, the volume of the gas core is 50 to 60% of the overall volume of the suspension. In another embodiment, lower volume percentages are preferred. Microbubble suspensions containing less than 50% gas (by volume), may be useful when resuscitation is desired in trauma, or in microvascular flaps being treated with microbubbles.

E. Size

The overall diameter of the microbubbles is selected to provide a high surface area to volume ratio, thereby favoring rapid transfer of the gas out of the microbubbles. For delivery of oxygen to a patient, typically, the microbubbles have diameters of about 20 microns or smaller, preferably the upper limit for the diameter of the microbubbles ranges from 15 microns or smaller, or 10 microns or smaller in order to pass through the pulmonary capillary bed following intravenous injection.

Preferably, the lipid monolayer is quite thin (e.g. about 10 nm), and the volume of the gas core comprises 90% or more of the overall volume of the microbubble, typically comprises between 99.00 to 99.99% of the overall volume of the microbubble.

F. Stability of Microbubble Suspensions

Microbubbles containing oxygen in their gas core may coarsen and break down by ripening (transfer of oxygen from a smaller particle to a larger particle due to differences in Laplace pressures) or by microbubble coalescence. The rate at which both of these processes occur is inversely proportional to the envelope cohesiveness, which increases with increasing lipid packing density and increasing lipid acyl chain length. Other factors, such as suspension viscosity, temperature and concentration of oxygen and other gases in the suspension may also affect stability.

The microbubbles described herein may be designed to be used immediately following production. In these embodiments, the microbubbles are relatively unstable, such as for only a few hours following production.

In other embodiments, the microbubbles are stable in storage for weeks to months at room temperature and standard pressures (e.g. 1 atm) or at lower temperatures, such at refrigeration at 4° C.

II. Methods of Making the Microbubble Compositions

Any suitable method for forming the microbubbles, or precursors for the microbubbles, may be used. Gas-filled microbubbles form by the adsorption of lipid components in the precursor suspension to the gas liquid interface of entrained gas bodies. This adsorption is generally accomplished by high energy conditions, such as amalgamation (intense shaking) or sonication. Other methods of gas injection may be used to form microbubbles, such as flow focusing, T-junctions or electrohydrodynamic atomization.

Formation of concentrated microparticle suspensions requires four general steps: (1) generation of the precursor suspension, (2) dispersion of the gas into the precursor suspension to form microbubbles, (3) concentration of the microbubble suspension and (4) size isolation to form a concentrated microbubble suspension with microbubbles having diameters below a selected upper size limit.

The microbubble suspensions may be formed on-site, just prior to administration. Alternatively the microbubble suspensions may be formed and stored for a suitable period of time and then used when needed.

A system for rapidly delivering oxygen to a patient in need thereof typically includes (a) means for generating a microbubble suspension, and (b) means for administering microbubbles continuously or discontinuously to a patient, tissue or organ in need thereof. Means for generating microbubble suspensions include sonicator and mechanical agitators, as described below. The microbubble suspensions can be administered via injection or by continuous infusion or by any other suitable means.

A. Methods for Forming Microbubbles

Typical methods of forming microbubbles and microbubble precursors are known in the art. These methods generally include the first two steps listed above and may include additional steps.

For example, microbubbles may be formed by mixing the lipids, i.e. base lipid(s) and PEGylated lipids, in a suitable organic solvent, such as chloroform; then evaporating the solvent to form a dry lipid film, and resuspending the lipid film in an aqueous medium and sonicating to form microbubbles. (see e.g. U.S. Pat. No. 7,105,151 to Unger et al.)

Alternatively, as disclosed in EP 0 077 752 to Schering AG, suspensions of gas microbubbles can be made by mixing an aqueous solution of a surfactant with a solution of a viscosity enhancer as a stabilizer. The gas bubbles are then introduced into the mixture by forcing the mixture of reagents and air through a small aperture. Similarly, suspensions of gas microbubbles can be formed by dissolving each of the lipids in an aqueous solution, such as sterile phosphate-buffered saline or sterile saline; then mixing the individual lipid solutions in the desired molar ratio to form a precursor solution, next the gas can be added to the precursor solution by any suitable means, including injecting the gas into a sealed container containing the precursor solution and agitating the solution to form microbubbles. The desired gas or mixture of gases, e.g. oxygen gas, may be perfused through the precursor suspension, thereby oxygenating the precursor solution.

Formation of microparticles is optimal when the suspension is kept cool. Thus, preferably the precursor suspension is cooled by suitable means.

Mechanical agitation has been the main method to create encapsulated microbubbles for biomedical applications, since their inception by Feinstein et al. Feinstein, et al., "Microbubble Dynamics Visualized in the Intact Capillary Circulation", *J. Amer. College of Card.*, 4(3): 595-600 (1984). Mechanical agitation is a common emulsification procedure in which a hydrophobic phase (i.e., gas) is dispersed within an aqueous surfactant solution by disruption of the interface. Shaking a serum vial with a device similar to a dental amalgamator may be used to for oxygen microbubbles.

Acoustic emulsification (i.e. sonication) may also be used to agitate the precursor solution and form microbubbles. Sonication generates large quantities of microbubbles (100 mL×$10^{10}$ mL$^{-1}$) rapidly and reproducibly within just a few seconds. In sonication, the sonicator horn is typically placed at the suspension-gas interface. The precursor suspension is sonicated for a sufficient time period at a sufficient power to produce the microbubbles. Microbubbles created in this way follow a heterogenous size distribution.

The largest microbubbles are the most buoyant and rise to the top of the suspension, while less buoyant, smaller microbubbles remain motile in the sonicated suspension. This allows for separation based on different migration rates in a gravitational field.

B. Concentration of the Microbubble Suspension and Size Isolation

In a bench scale operation, microparticle suspensions are pumped out via a port at the bottom of the glass beaker and into a sterile syringe.

To continue production of the microbubbles, another pump simultaneously replaces fresh precursor suspension into the top of the glass beaker. Unprocessed microbubble suspensions created in this way typically contain 8-10 mL oxygen per dL of suspension. The amount of oxygen in the microbubble suspensions can be increased by centrifugation.

A rapid and simple method for concentrating and isolating sub-populations of lipid coated microbubbles has been developed. This method involves the use of differential centrifugation to isolate size-selected microbubbles based on their migration in a centrifugal field.

The relative centrifugal force (RCF) needed for a microbubble size class to rise through the column of length L for a fixed centrifugation time can be calculated. For example, Stokes' equation for the rise velocity of a buoyant particle relative to the bulk fluid under creeping flow conditions can be used as follows:

$$u_i = \frac{2(\rho_2 - \rho_{1i})}{9\eta_2} r_i^2 g, \quad \text{(Eq. 1)}$$

where subscript i refers to the microbubble size class, $r_i$ is the microbubble radius and g is the gravitational (centrifugal) acceleration measured in RCF. (see Kvale, et al., "Size fractionation of gas-filled microspheres by flotation", *Separations Technology*, 6(4):219-226 (1996)). The effective viscosity, $\eta_2^*$, of the microbubble suspension can be calculated using Batchelor and Greene's correlation for the modified fluid viscosity:

$$\frac{\eta_2^*}{\eta_2} = 1 + 2.5\Phi + 7.6\Phi^2, \quad \text{(Eq. 2)}$$

$$\Phi = \sum_{i=1}^{N_d} \Phi_i, \quad \text{(Eq. 3)}$$

where $\Phi$ is total the microbubble volume fraction for $N_d$ size classes. (Batchelo & Green, "Determination of Bulk Stress in a Suspension of Spherical-Particles to Order C-2", *J. of Fluid Mech.*, 56: 401-427 (1972).) Equations 1-3 can be used to calculate the strength of the centrifugal field (in RCF) for a given initial size distribution, time period and syringe column length.

Then the centrifuge is run at the rate calculated above to remove the largest microbubbles, e.g. greater than 20 microns, greater than 15 microns, or greater than 10 microns. For example, to remove microbubbles having diameters greater than 10 microns, the sample may be run for one cycle at 30 RCF for 1 min. Then the cake is discarded, and the infranatant which contains the smaller microbubbles is saved.

If smaller microbubbles are desired, the infranatant is redispersed in an appropriate volume of diluent, such as PBS. Then the centrifuge can be run at a higher speed, as calculated above, to remove the large microbubbles from the sample.

Using this method, the amount of gas (e.g. oxygen) in the microbubble suspensions can be increased 4-fold to 10-fold, or by even greater amounts. For example, an unconcentrated suspension which contained 8-10 mL oxygen per dL of suspension, was concentrated to produce a microbubble suspensions with between 40 and 90 mL per dL of suspension.

1. Size Measurements

The size of the microbubbles can be determined by any suitable device, such as an Accusizer® or a Multisizer® III. While the Accusizer® measures size based on light obscuration and scattering, the Multisizer® utilizes electrical impedance sensing of the volume of electrolyte displaced by the microbubble as it passes through an orifice.

Microscopy can be used for direct visual inspection of the microbubbles in the suspension.

Flow cytometry can be used to further characterize the polydisperse microbubbles. Forward- (FSC) and side- (SSC) light scattering measurements can be taken. These measurements can also be used to correlate the data obtained using the Accusizer® or Multisizer® III to better understand the size distribution of the microbubbles.

III. Kits for Delivering Oxygen

A kit for rapidly delivering oxygen to a patient in need thereof may contain one or more lipids and one or more emulsifying agent for forming microbubbles, a pharmaceutically acceptable carrier, and a source of oxygen. These components can be combined to form the microbubbles described herein. The resulting microbubbles contain a lipid envelope and a gas core. The gas core contains oxygen. The lipid envelope contains one or more lipids in the form of a lipid film and one or more emulsifying agentsThe outer surface of the lipid film forms a protective border. The one or more emulsifying agents contains a group or molecule that forms the protective border, typically a hydrophilic polymer (e.g. PEG). The suspension of microbubbles contains at least 40% oxygen by volume.

Preferably the kit contains instructions for forming the microbubbles and for administering the microbubbles to a patient, tissue or organ in need thereof.

The components in the kit are preferably provided in sterile packaging.

IV. Uses for the Microbubbles

The microbubbles may be administered to any patient, tissue or organ in need of an increase in oxygen concentration in their blood, tissue or organ. The microbubbles may be administered alone or in combination with other treatments as an adjunctive therapy.

Fully saturated whole blood with physiologic hemoglobin contains 20 mL oxygen per dL. Microparticle suspensions can be manufactured to contain between 40 and 70 mL oxygen per dL of suspension. Thus, the injection of one dL of suspension can deliver about 40-70 mL of oxygen directly to a tissue or organ in need of immediate oxygenation.

In preferred embodiments, the microbubbles contain oxygen and are administered to patients experiencing local or systemic hypoxia. Hypoxic or ischemic conditions may arise in a patient as a result of a variety of mechanisms, including, but not limited to, congenital physical or physiologic disease or disorders, embolisms, including thromboembolisms, peripheral artery occlusive disease, transient ischemic attacks, strokes, acute trauma, surgical interventions, or exposure to chemical or environmental agents. The microbubbles are administered in an effective amount and at suitable rate for increasing or maintaining the $PO_2$ in a patient following administration. Typically, the microbubbles are administered in an effective amount and at suitable rate to deliver an effective amount of oxygen to a patient to ischemic tissues or to desaturated blood in a time ranging from 0.5 to 30 seconds following administration, wherein the amount of oxygen that is delivered is effective to restore $PO_2$ levels to normal levels or prevent or alleviate ischemic injury. Microbubbles providing immediate release of oxygen are particularly preferred for acute resuscitations and resuscitation the heart of a patient.

In another embodiment the microbubbles provide sustained release of oxygen. Such microbubbles may be used to deliver oxygen to the brain and other tissues.

Hemorrhagic Shock and Other Trauma Applications

In acute hemorrhage, resuscitative trauma therapy focuses upon restoration of circulating blood volume and oxygen carrying capacity. In states of hypovolemic shock, such as resulting from severe blood loss, the oxygen extraction ratio of peripheral tissues is increased. The result is further desaturation of blood returning to the right heart. Models of blunt chest trauma and hemorrhagic shock have suggested that right ventricular (RV) dysfunction impedes resuscitation efforts.

In late hemorrhagic shock, myocardial ischemia causes impaired contractility. Volume resuscitation of an ischemic, dysfunctional right ventricle may lead to increased RV end-diastolic volume, causing septal shift into the left ventricle (LV), and decreased LV end-diastolic volume.

The microbubble suspensions can be injected at an appropriate concentration and rate to deliver oxygen directly to the myocardium in a time period ranging from 3 to 10 second following injection. For example, if the microbubble suspensions contains from 40 to 70 mL oxygen per dL of suspension, the injection of one dL of suspension could deliver approximately 40-70 mL of oxygen directly to the myocardium.

Optionally, the microbubble suspension may contain a specialized resuscitation fluid, such as synthetic colloid (e.g. Hextend®) or hemoglobin-based oxygen carrier (HBOC) as the carrier. When the microbubbles deliver oxygen directly to ischemic tissues, they would leave behind their PEG-rich lipid shell (which exhibits favorable oncotic properties) and carrier, serving as a volume expander.

Microbubbles as an Adjunctive Therapy

Oxygen-carrying microparticle suspensions are a useful adjunctive therapy in traumatic injury for several reasons.

In patients with airway failures, injectable microbubbles provide a route of oxygen administration which allows survival of previously lethal injuries, such as wounds involving the airways and those causing severe lung injury. Oxygenated microbubbles provide a highly portable form of intravenous oxygen which may be used to rescue such patients, allowing them to be transported to definitive therapy without ischemic injuries to other organs.

In patients with cardiac arrest, whether traumatic, ischemic or otherwise, successful resuscitation depends upon establishing a patent airway, ventilating the patient with high oxygen concentrations and adequate chest compressions to provide active pulmonary blood flow. All of these interventions must be in place in order to raise coronary arterial oxygen content to maximize the likelihood of return of spontaneous circulation. Intravenous administration of the microbubbles containing oxygen may provide a bolus of oxygen to the right side of the heart, in an effective amount to improve right heart function via endocardial oxygen delivery, improve pulmonary arterial perfusion and delivery of blood to the left side of the heart compared to no intravenous administration of the microbubbles. Even prior to restoration of appropriate mechanical ventilation, microbubbles administered via intravenous injection can traverse atelectatic lung and perfuse the left heart. The microbubbles may be delivered to the left heart in an effective amount to decrease time to return of spontaneous circulation and improve outcomes in cardiac arrest.

In patients with hemorrhagic shock, in the low cardiac output state, an intravenous injection of rapidly dissolving oxygen microbubbles targets the myocardium (the first place the microbubbles reach) and delivers the gas core to surrounding endocardium. As shown in the animal studies described in the Examples, the microbubbles can deliver an effective amount of oxygen to rapidly improve cardiac output compared to no treatment and serve as an adjunct therapy to volume repletion.

A concentrated suspension of microbubbles may be added directly to existing volume expanders in the field, which may improve cardiovascular and cerebral resuscitation. This may serve as a useful adjunctive therapy to rescue patients with severe hemorrhagic shock, when myocardial ischemia leads to dysfunction, inadequate pulmonary blood flow and systemic desaturation. The microbubble suspensions can be design to be stable for extended periods of time, ranging from days to weeks.

Microvascular Operations

Microbubbles having diameters of less than 5 microns in a diluent such as Dextran may be administered via direct intraarterial injection. Microbubbles that are infused towards at-risk tissues or a recent microvascular operation, may deliver an effective amount of oxygen to improve rheology and oxygen content of the perfusate, and thereby improve oxygen delivery in these settings.

As a corollary, in circumstances of focal low flow states, such as near-amputations, microbubbles with prolonged bloodstream persistence, such as from about 15 to about 45 seconds following administration, may be designed such that they circulate in vivo until local conditions favor diffusion of oxygen from the microbubble core into ischemic tissues (i.e. when they are surrounded by a hypoxemic milieu). Because the oxygen content of microparticle suspensions upon injection is greater than that of saturated whole blood (40-60 mL $O_2$/dL suspension vs. 20 mL $O_2$/dL blood), continuous microbubble infusions may be used to raise the oxygen content of circulating blood.

Carbon Monoxide Poisoning

Oxygenated microbubble suspensions carry within them high concentrations of oxygen. As such, they may be effective in displacing hemoglobin scavengers, such as carbon monoxide. In cases of severe carbon monoxide poisoning, circulating microbubbles could deliver oxygen directly to the tissues in an effective amount to improve hemoglobin function, providing a portable temporizing therapy for patients with impaired hemoglobin function.

Traumatic Brain Injury

Infusion of oxygen-bearing microbubbles into the cerebral circulation may decrease neuronal death at the ischemic penumbra. Given the improved oxygen content of microbubble suspensions over that of whole blood, patients with impaired cerebral blood flow, e.g. in traumatic brain injury or intracranial hypertension, directed administration of oxygenated microbubbles into a carotid artery would increase the oxygen content ($CaO_2$) of blood flow directed to the brain, and may balance the decrease in flow with an improvement in oxygen content. Microbubbles may be mixed in a buffered, low viscosity solution (e.g. THAM) and may contain antioxidants and other factors known to mitigate neuronal injury (e.g. DHA). The polyethylene glycol moiety of the lipids utilized in the microbubble envelope exerts significant oncotic pressure, which may decrease vasogenic edema.

Cyanotic Congenital Heart Disease

A unique feature of congenital heart disease is partial or complete mixing of saturated and desaturated blood. In perioperative states, systemic desaturation can lead to significant cerebral and myocardial dysfunction. For example, frequently patients with hypoplastic left heart syndrome require extracorporeal life support in the perioperative period primarily to prevent death due to hypoxemia and the concomitant myocardial dysfunction. ELSO. Extracorporeal Life Support Registry Report, International Summary; 2008 January, 2008.

Microbubbles containing oxygen may be administered intravenously in an effective amount to raise mixed venous oxygen content, systemic oxygen content, and improve myocardial function in patients in a perioperative states. Thus the microbubbles can be administered in place of a more invasive use of extracorporeal life support device.

Pulmonary Hypertension

Pulmonary hypertension remains a health care problem with few effective therapies. Oxygen is known to be a potent pulmonary vasodilator. Thus, the microbubbles containing oxygen may be administered intravenously in an effective amount to raise the oxygen content in pre-capillary pulmonary arterioles and improve pulmonary vasodilation compared to no treatment in patients with pulmonary hypertension.

Acute Respiratory Distress Syndrome (ARDS)

Refractory hypoxemia is the hallmark of acute lung injury and ARDS.

Profound hypoxemia accounts for 10% of the mortality of this common disorder. Meade et al., "Ventilation strategy using low tidal volumes, recruitment maneuvers, and high positive end-expiratory pressure for acute lung injury and acute respiratory distress syndrome: a randomized controlled trial." JAMA, 299(6):637-45 (2008). Microbubbles containing oxygen may be administered intravenously in an effective amount to alleviate the hypoxemia associated with severe intrapulmonary shunting and decrease the mortality and morbidity of ARDS.

Delivery of Microbubbles to Fetuses, Neonates and Infants

The microbubbles may be administered to a fetus, neonate, or infant in need of additional oxygen. The microbubbles may be administered to low birth weight infants or premature infants. In one embodiment, the microbubbles are administered in an effective amount to ensure that the fetus, neonate, or infant is receiving sufficient oxygen, particularly to ensure that the brain of the fetus, neonate or infant receives sufficient oxygen for development and maintenance of normal function.

If a mother is experiencing preeclampsia, the baby must be born. Optionally, the microbubbles can be administered to the baby, mother, or both in effective amount to deliver an effective amount of oxygen to maintain normal normal bodily functions when the mother is experiencing preeclampsia.

Neonates with hypoxic ischemic brain injury at the time of birth often suffer from extensive brain injury, manifested as cerebral palsy. This may occur due to even brief periods of hypoxia during the peripartum period. In clinical situations where this is appreciated prior to delivery, such as a nuchal cord or placental abruption, injection of microbubbles into the umbilical circulation or into the dural space may avert critical hypoxia and may ameliorate some forms of hypoxic ischemic brain injury in this setting.

Delivery of Other Medical Gases

In another embodiment, the gas contained within the microbubbles may be a biologically useful gas other than oxygen, including, but not limited to, nitric oxide, and volatile anesthetics, such as isoflorane.

Volatile anesthetics may be included in the gas core in the microbubbles described herein in place of, or in addition to, oxygen. In this embodiment, the microbubbles may be administered in an effective amount to serve as a sedative, antiepileptic drug or bronchodilator. For example, microbubbles containing isoflorane in place of oxygen can be delivered to diseased airways from the pulmonary capillary to the distal bronchioles. Administration of microbubbles containing isoflorane may be used as an adjunctive therapy for treatment of patients with severe asthma.

Microbubbles containing nitric oxide, a pulmonary vasodilator, in the gas core in place of oxygen may be administered to patients in an effective amount to deliver this pulmonary vasodilator to pulmonary arterioles and alleviate pulmonary vasodilation.

Finally, microbubbles containing antiepileptic drugs in the gas core in place of oxygen can be manufactured, such as by using the methods described herein, to have sizes suitable for crossing the blood-brain barrier. The microbubbles can be used to deliver doses of drug that are lower than the standard systemic dose of the antiepileptic drug yet achieve the same effect. Microbubbles containing antiepileptic drugs in the core may administered to patients in need of treatment in an effective amount to improve delivery of these drugs to epileptogenic areas and minimize adverse effects associated with systemic administration of higher doses of the drug.

B. Methods of Administration

The compositions containing microbubble suspensions may be administered locally or systemically, depending on the condition to be treated. The compositions are typically administered via injection. In some embodiments the compositions can be administered as continuous infusions. In some embodiments the compositions are administered intravenously or intraarterially. In others, the compositions are administered directly to the tissue or organ in need of treatment.

In one embodiment, the microbubble suspensions are stable in storage for prolonged periods of time, and may be withdrawn and directly injected without further alterations of the solution.

In another embodiment, the microbubbles may be formed just prior to administration, e.g. within seconds or minutes of injection, by a suitable device. The methods disclosed herein allow for rapid production of oxygen-containing microbubbles for use in clinical settings or in the field.

C. Rates of Administration

The volume of the gas-filled microbubble suspension to be administered is a function of a number of factors including, the method of administration, the gas percentage of the microbubble suspension, and the age, sex, weight, oxygen or carbon dioxide tension, blood pressure, systemic venous return, pulmonary vascular resistance, and physical condition of the patient to be treated.

The whole body oxygen consumption of an adult at rest is approximately 200 mL oxygen per minute. Thus, in the setting of an acute airway obstruction, for example, infusion of 200 mL/minute of oxygen would prevent critical ischemic injury. For example microbubble suspensions containing 70 mL/dL of suspension can be administered at 285 mL/minute to transfer 200 mL/minute of oxygen in vivo. Since most of the suspension contains oxygen gas, most of the volume decreases following administration and release of the gas. Values of co-administered volumes for physiologically relevant oxygen demands are shown below in Table 1. Additionally, when used in the setting of an acute resuscitation or in organ-targeted oxygen delivery, volumes of co-infusate may be much lower. For example, a 10 mL bolus of 50% (volume gas/volume suspension) microbubbles in adults may provide a suitable amount of oxygen to improve the survival of the organ.

TABLE 1

List of Administration Rates for Carrier and Lipids to Administer 100 mL/min or 200 mL/min of Oxygen

|  | $O_2$ Delivery | 70 Vol % | 90 Vol % |
|---|---|---|---|
| Carrier | 100 mL/min | 30 mL/min | 10 mL/min |
| Volume | 200 mL/min | 60 mL/min | 20 mL/min |
| Lipid Volume | 100 mL/min | 0.054 mL/min | 0.054 mL/min |
|  | 200 mL/min | 0.108 mL/min | 0.108 mL/min |

D. Gas Release

The microbubbles are preferably designed to release the gas encapsulated therein quickly following administration in vivo. Typical release times range from 0.5 seconds to 1 minute, with shorter time periods, such as from 0.5 to 30 seconds, more preferably from 0.5 to 10 seconds, being preferred for acute resuscitations and resuscitations of the heart and with longer time periods being preferred for delivery of oxygen to the brain.

In some embodiments, the microbubbles are designed to persist in vivo until they reach hypoxic tissue, at which time they will release the encapsulated oxygen and the lipid envelope with collapse.

As oxygen is released and the encapsulating envelope collapses, the lipid material sheds as micelles and vesicles, typically having sizes ranging from 10 nm to 100 nm, which then undergo hepatic metabolism. Due to the small size of the lipid film relative to the radius of the microbubble, the effective volume of lipid is approximately one thousandth of one percent of the volume of suspension.

The lipid material does not persist in vivo for a sufficient time to carry carbon dioxide or other gases to the lungs. The microbubbles generally release the encapsulated gas and the gas is absorbed by hemoglobin prior to the first circulation into the pulmonary vasculature. In a healthy adult patient with a normal cardiac output, the release of the encapsulated gas typically occurs from 4 to 5 seconds following injection, or faster.

The present invention will be further understood by reference to the following non-limiting examples.

EXAMPLES

Example 1

Formation of Concentrated Microbubble Suspensions

Concentrated microparticle suspensions were formed using the following four main steps: (1) generation of the precursor suspension, (2) sonication, (3) concentration and (4) size isolation.

1. Generation of precursor suspension. Microparticle suspensions using each of the lipids listed in Table 2 below were created. The base lipids were received in powder form (Avanti Polar Lipids, Alabaster, Ala.) and dissolved in sterile saline to create a stock solution. The same was done with PEGylated lipid. Base lipids were mixed with the PEGylated lipid in a 95:5 molar ratio. The final concentration of each precursor solution was 3 mg total lipid/mL. Lipid precursor solutions were stored at 4° C.

TABLE 2

List of Base Lipids and PEGylated Lipids with Transition Temperature ($T_m$) and Reduced Temperature ($T_R$)

| Microbubble Lipid Components | Abbreviation | $T_m$ (° C.) | $T_R$ at 25° C. | $T_R$ at 37° C. |
|---|---|---|---|---|
| Base Lipids | | | | |
| 1,2-Dilauroyl-sn-Glycero-3-Phosphocholine | C12 | −1 | 1.10 | 1.14 |
| 1,2-Dimyristoyl-sn-Glycero-3-Phosphocholine | C14 | 23 | 1.01 | 1.05 |
| 1,2-Dipentadecanoyl-sn-Glycero-3-Phosphocholine | C15 | 33 | 0.97 | 1.01 |
| 1,2-Dipalmitoyl-sn-Glycero-3-Phosphocholine | C16 | 41 | 0.95 | 0.99 |
| 1,2-Distearoyl-sn-Glycero-3-Phosphoethanolamine | C18 | 55 | 0.91 | 0.95 |
| 1,2-diarachidoyl-sn-glycero-3-phosphocholine | C20 | | | |
| 1,2-didocosanoyl-sn-glycero-3-phosphocholine | C22 | | | |

TABLE 2-continued

List of Base Lipids and PEGylated Lipids with Transition Temperature ($T_m$) and Reduced Temperature ($T_R$)

| Microbubble Lipid Components | Abbreviation | $T_m$ (°C.) | $T_R$ at 25° C. | $T_R$ at 37° C. |
|---|---|---|---|---|
| PEGylated Lipid | | | | |
| 1,2-Dimyristoyl-sn-Glycero-3-Phosphoethanolamine-N-[Methoxy(Polyethylene glycol)-550] | 14:0PE-PEG | N/A | N/A | N/A |

2. Sonication. Gas-filled microbubbles self-assemble to form lipid monolayers when lipid precursor suspensions are mixed with a gas under high energy conditions.

Figure 2:
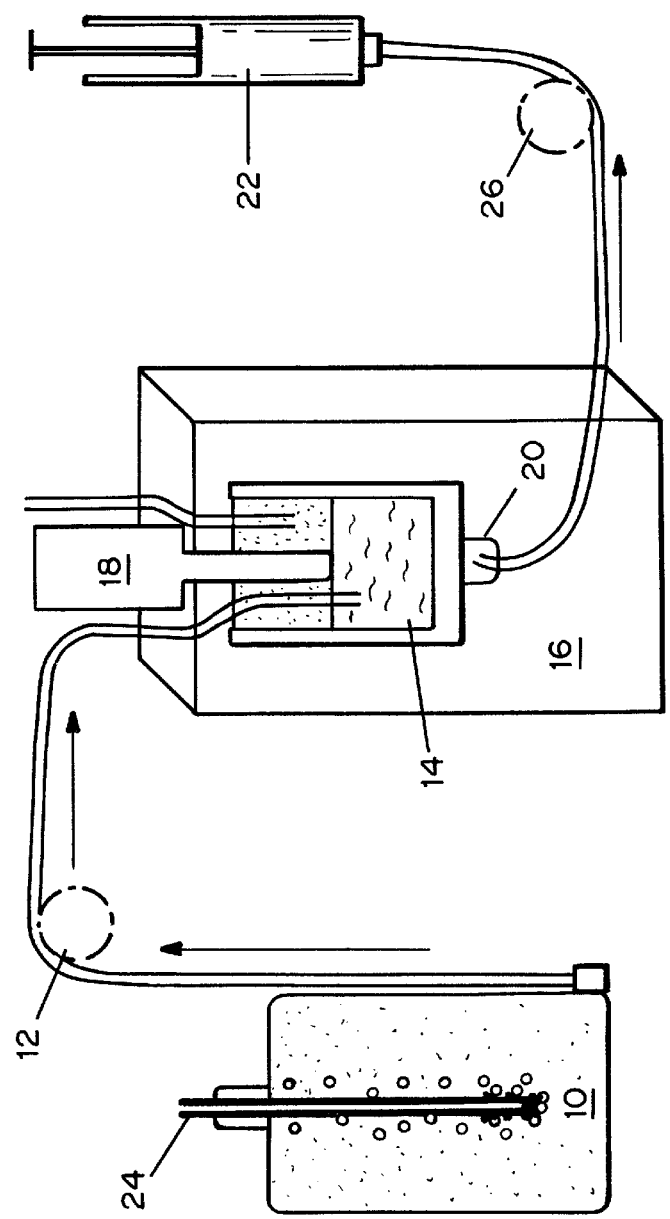
FIG. 2 is a schematic of a bench-top method for forming microbubbles.

A schematic of the instrumentation used for the sonication step is illustrated in FIG. 2.

As shown in FIG. 2, precursor suspensions were stored in a large glass container (10) through which oxygen gas was perfused, oxygenating the precursor solution. This solution was then moved via roller pump (12) into a beaker (14) surrounded by a cold water bath (Radnoti Glass Technology, Monrovia, Calif.) (16), which counters the heat created by the sonicator. Formation of microparticles is optimal when the suspension is kept cool. The sonicator (Branson Sonifier 250A, Branson Ultrasonics, Danbury, Conn.) was operated continuously at maximal power. The ⅝" sonicator horn (18) was placed at the suspension-gas interface. Pure oxygen gas was flowed continuously over the suspension at 6 liters per minute, creating a pure oxygen hood. The sonicator was maintained within a sound enclosure.

Microbubbles formed in this way follow a heterogenous size distribution. The largest microbubbles are the most buoyant (macrobubbles), which rise to the top of the suspension. Smaller microbbles are less buoyant and remain motile in the sonicated suspension. Microbubble suspensions were pumped out via a port (20) at the bottom of the glass beaker and into a sterile syringe (22). Another roller pump (not shown in FIG. 2) simultaneously replaced fresh precursor suspension into the top (24) of the glass beaker (10). This method allowed for the formation of 300 mL/minute of fresh microbubble suspensions.

The oxygen content of the microbubble suspension was measured as follows. A syringe was filled with a known volume of microparticles. The difference in weight of the filled syringe from that of the empty syringe was divided by the density of the precursor suspension, estimating the volume of fluid in the syringe. The remainder of the volume may be assumed to be gas, which is weightless. This method is referred to herein as the "Oxygen Content Determination Method". Unprocessed microbubble suspensions created in this way contained 10-20 mL oxygen per dL of suspension.

3. Centrifugation. Unprocessed microbubble suspensions were gathered in a batch of 60 mL syringes (Beckton-Dickenson) which were modified by shortening the plungers, so that the syringes could fit in a centrifuge (Beckman table top centrifuge). Syringes were directly filled via pressure from the pump (26) (see FIG. 2), and were sealed with a cap following removal from the system described above. Each batch of 16 syringes were then placed in the centrifuge for 4 minutes at 500×G. This force separated macrobubbles (least dependent), with diameters greater than about 20 to 30 microns, from smaller microbubbles (intermediate), with diameters up to about 20 microns, from infranatant lipid solution (most dependent). After infranatant portions were recycled into the precursor solution, the thin, heterogenous microbubble layers inside of each syringe were combined into one 60 mL syringe using a T connector. When sized optically, these particles were heterogenous in size, ranging from 5-30 microns in diameter (see FIG. 4, gray line).

Figure 4:
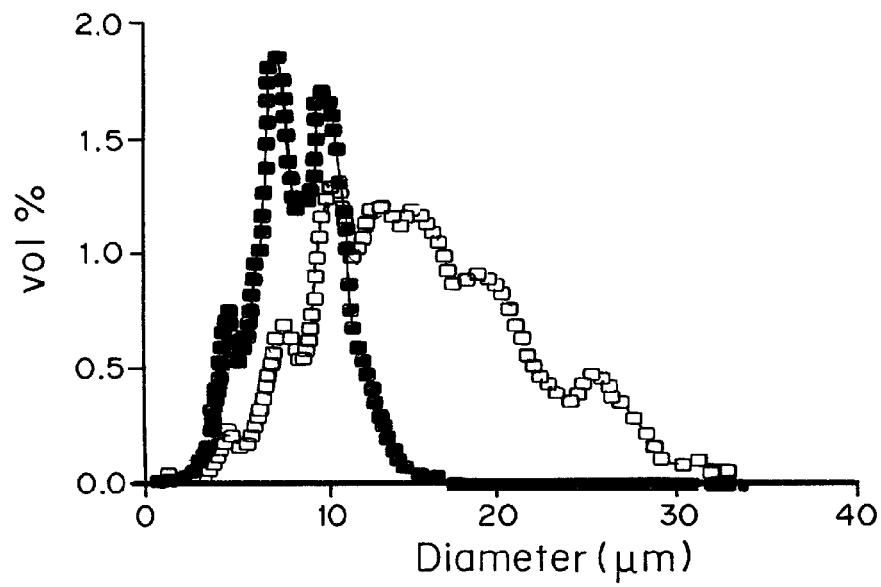
FIG. 4 is a graph of size distribution for the microbubbles, plotting percent volume versus diameter (μm), as determined by optical sizing following gentle centrifugation (gray line) and following an isolation process (black line).
Figure 5:
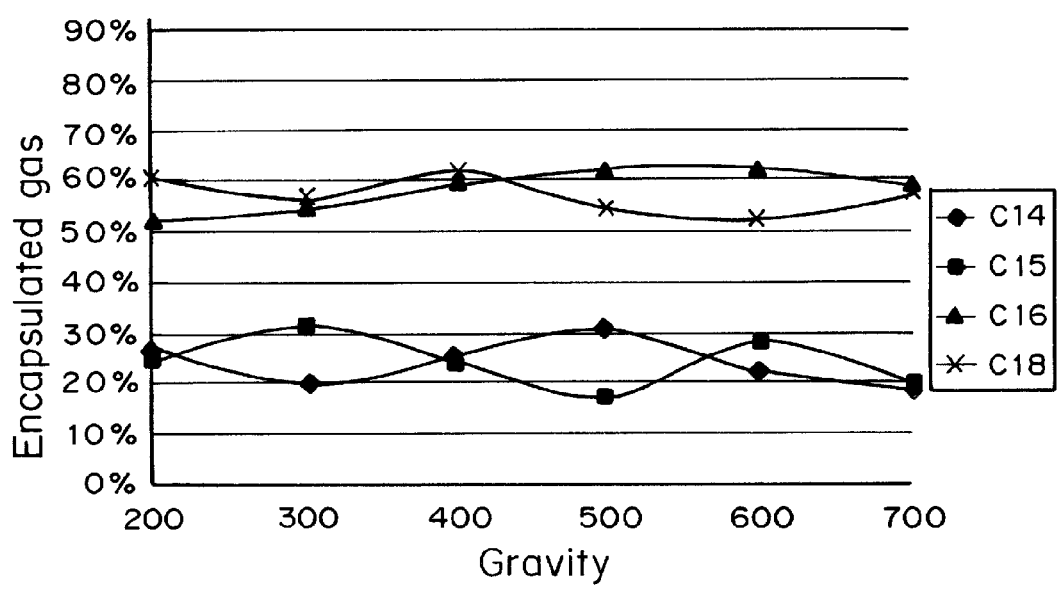
FIG. 5 is a graph of percentage of encapsulated oxygen (% of total volume) of microbubbles with four different acyl chain lengths (C14, C15, C16 and C18) following six serial centrifugations at varying speeds (expressed as multiples of gravity force). The data is plotted as percentage of encapsulated oxygen versus speed (amount×Gravity), with C14 represented by a diamond, C15 represented by a square, C16 represented by a triangle and D18 represented by an "x".

The ability to withstand centrifugation and create a concentrated microparticle suspension is a function of microbubble acyl chain length (see FIG. 5). As shown in FIG. 5, the microbubbles formed with lipids with longer acyl chain lengths (e.g. 1,2-Dipalmitoyl-sn-Glycero-3-Phosphocholine and 1,2-Distearoyl-sn-Glycero-3-Phosphoethanolamine) encapsulated greater volumes of oxygen than those formed from lipids with shorter acyl chains (e.g. 1,2-Dimyristoyl-sn-Glycero-3-Phosphocholine and 1,2-Dipentadecanoyl-sn-Glycero-3-Phosphocholine). The microbubbles formed with C16 and C18 lipids as the base lipids contained 50-60% oxygen in the concentrated suspension (see lines containing triangles (C16) and "x" (C18) in FIG. 4. In contrast, the microbubbles formed with C14 and C15 lipids as the base lipids contained only 20-20% oxygen in the concentrated suspension (see lines containing circles (C14) and squares (C15) in FIG. 5). The oxygen content of the microbubble suspensions was determined using the Oxygen Content Determination Method described above. It is expected that microbubbles formed of lipids with longer acyl chains will obtain the same amounts or even greater amounts of oxygen following the concentration step.

4. Size Isolation. To isolate the desired particle sizes, 40 mL concentrated particles were resuspended in 20 mL of oxygenated saline in a 60 mL syringe. The syringe was left in an inverted position for 10 minutes at room temperature. Microbubbles layer themselves according to the Stokes approximation for the velocity reduction of a moving sphere due to viscous drag in creeping flow. Using this technique, particles of less than 15 microns were isolated by capturing only the suspension in the inferior 6.8 cm of the syringe (total length of each syringe was 7.2 cm).

Following removal of the larger microbubbles, the remaining microbubbles were reconcentrated using a final, low speed centrifugation process (200×G). Results of a 15 micron isolation (following reconcentration) are shown in FIG. 4, black line.

This method was used to produce a concentrated microbubble suspension at a concentration of 80 mL oxygen per dL suspension by weight, as determined using the Oxygen Content Determination Method described above.

Example 2

Efficiency and Rate of Gas Transfer to Desaturated Human Hemoglobin

The base lipids used in the preparation of the microbubbles were 1,2-Dilauroyl-sn-Glycero-3-Phosphocholine; 1,2-Dimyristoyl-sn-Glycero-3-Phosphocholine; 1,2-Dipentadecanoyl-sn-Glycero-3-Phosphocholine; 1,2-dipalmitoyl-sn-Glycero-3-Phosphocholine; 1-Miristoyl-2-Palmitoyl-sn-Glycero-3-Phosphocholine; 1,2-Dimyristoyl-sn-Glycero-3-[Phospho-rac-(1-glycerol)]; and 1,2-Dimyristoyl-3-Trimethylammonium-Propane. The PEGylated lipid used in the microbubbles was 1,2-Distearoyl-sn-Glycero-3-Phosphoethanolamine-N-[Methoxy(Polyethylene glycol)-5000]. All lipids were purchased from Avanti Polar Lipids, Alabaster, Ala.

Venous whole blood was withdrawn from healthy donors and stored in heparinized syringes. The mean $PO_2$ of the venous blood was 52.1 mm Hg.

Formation of the Microbubble Suspensions

Each of the above listed lipids was dissolved in sterile phosphate-buffered saline via sonication at high power for 10 minutes, yielding a stable solution of dissolved, concentrated lipid. Base lipids were mixed with the PEGylated lipid in a 95:5 molar ratio to form a precursor solution. Each precursor solution was placed in a sealed beaker, the head space of which was made 100% oxygen by oxygen washout. A sonicator (Branson Sonifier Model 150, Danbury, Conn.) was used to sonicate each precursor solution for 5 seconds, yielding a rich oxygen-filled microbubble suspension. The microbubbles were withdrawn from the dependent portion of the beaker into a 60 mL syringe, avoiding the more buoyant macrobubbles which floated to the top. Alternatively, the microbubbles were withdrawn from the beaker via a roller pump, the affluent line of which was placed in the inferior-most position within the beaker.

Microbubble suspensions were infused at incrementally increasing rates: 0.2, 0.4, 0.6, 0.8 and 1 mL/min, while desaturated erythrocytes are infused at 5 mL/min. Infusions were run for two minutes at each rate, and the blood was collected in triplicate at each rate during in the final minute for analysis. Blood and microbubbles were mixed by convection in a circuit composed of gas-impermeable tubing (Tygon, FEP-lined tubing, Cole Parmer, Vernon Hills, Ill.). $PO_2$ of the blood was measured following at 1.5 mL of tubing, which represented approximately 3.8 seconds of mixing time. $PO_2$ was immediately measured by conventional blood gas techniques.

Figure 3A:
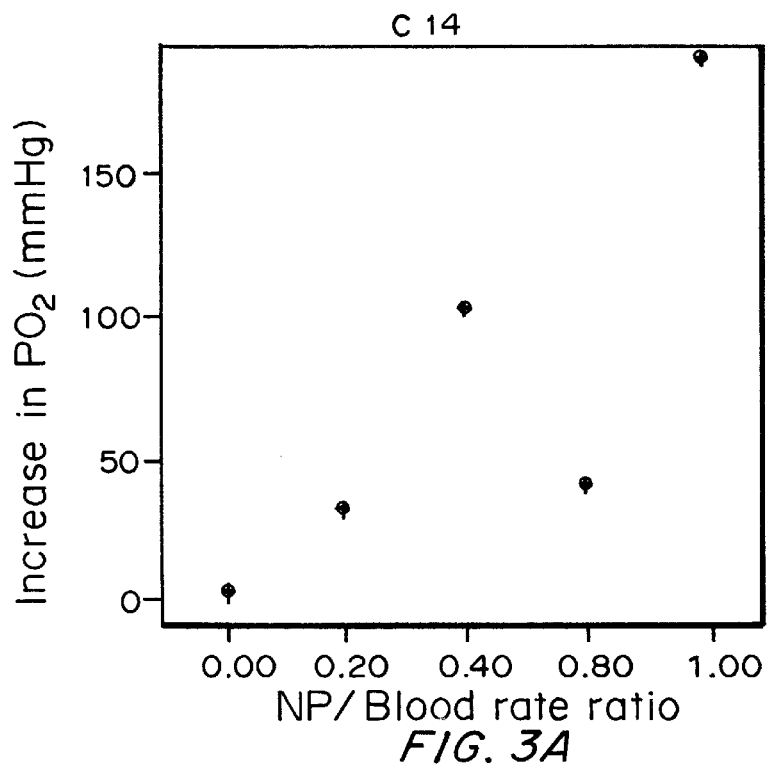
FIGS. 3 A, B, C, and D are graphs showing the mean increase in $PO_2$ above the control $PO_2$ (mm Hg) as plotted against the ratio of the rate of unconcentrated microbubble to the rate of blood infusion for each of four microbubble suspensions (C14 (FIG. 3A), C14:16 (FIG. 3B), C16 (FIG. 3C), and C18 (FIG. 3D)).
Figure 3B:
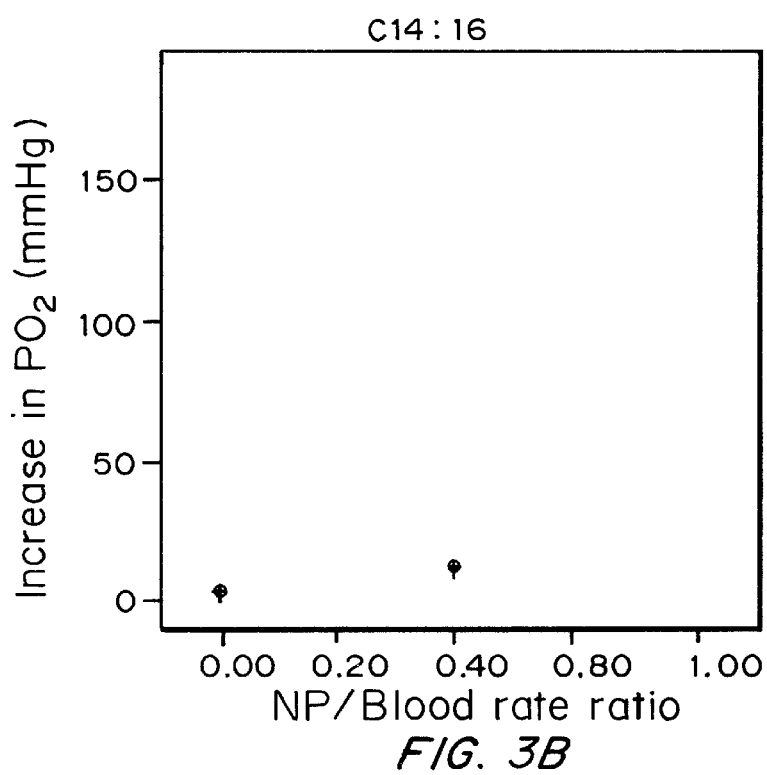
Figure 3C:
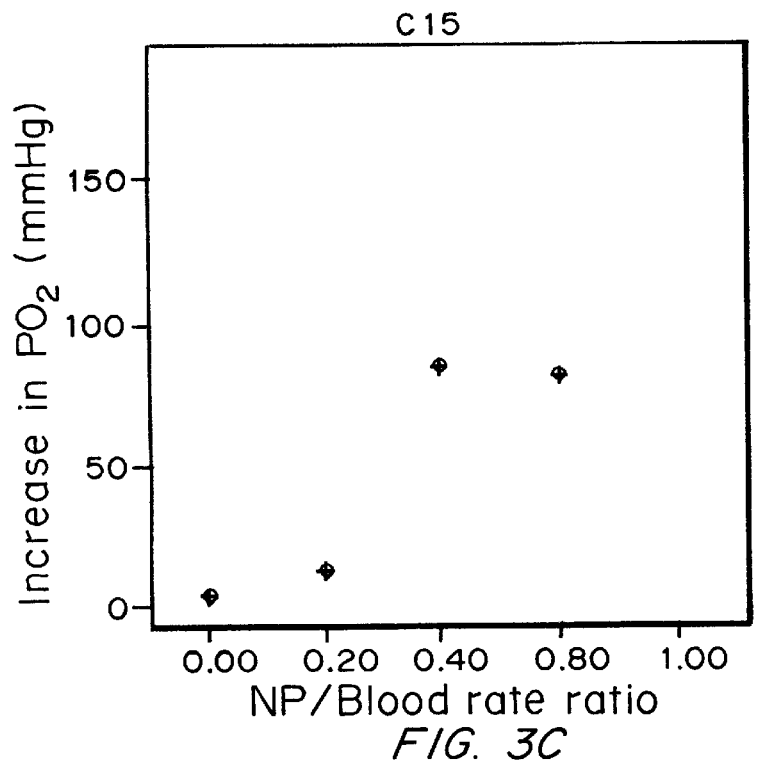
Figure 3D:
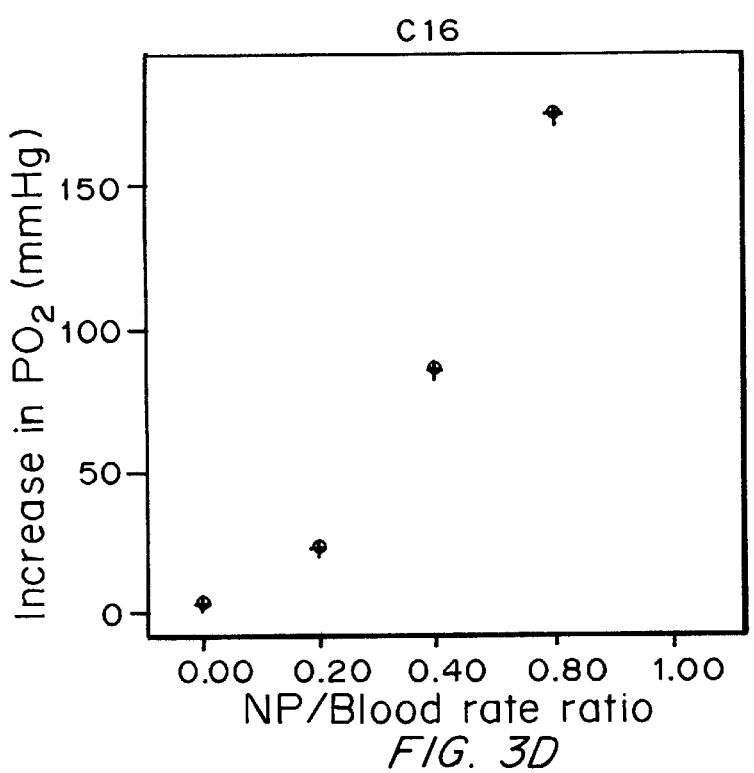

In FIGS. 3A, B, C, and D, the mean increase in $PO_2$ above the control $PO_2$ (mm Hg) is plotted against the ratio of the rate of unconcentrated nanoparticle to the rate of blood infusion for each of four nanoparticle suspensions tested. As shown in FIG. 3, C14 (p=0.01), C15 (p=0.07) and C16 (p=0.004) raised $PO_2$ above control rates to a statistically and clinically significant extent. C14-based particles increased $PO_2$ by 50 mmHg to greater than 500 mm Hg (depending upon infusion rate). C14:16 was ineffective in transferring oxygen. C18 displayed macroscopic evidence of nanoparticle persistence by way of visible nanoparticle suspension in the tubing (which is white and starkly contrasts blood) as well as microscopically.

Example 3

Comparison of Microbubbles Encapsulating Oxygen and Unencapsulated Oxygen in Desaturated, Venous Whole Blood Tested In Vitro The effect of oxygen-bearing microbubbles containing DPPC as the base lipid and PEG stearate as the emulsifying agent in a molar ration of 95:5 (base lipid:emulsifying agent), which were prepared according to the method of Example 1 without the concentration and size isolation steps, on a 2 mL sample of desaturated, venous whole blood from a healthy human volunteer was studied. In one test tube, 0.2 mL of the microbubbles were added to 2 mL of desaturated, venous whole blood. To a second test tube, 0.2 mL of pure oxygen gas (unencapsulated) was added to 2 mL of desaturated, venous whole blood.

The test tubes were inverted once, and co-oximetry and blood gas values measurements were taken using a Radiometer ABL800 X blood gas machine.

The test tube containing microbubbles had a pH of 7.31, $PCO_2$ of 50 mmHg, $PO_2$ of 248 mmHG, and the amount of oxygenated hemoglobin (oxyHb) was measured at 99.8%. In contrast, the test tube containing unencapsulated oxygen had a pH of 7.33, $PCO_2$ of 59 mmHg, $PO_2$ of 33 mmHG, and the amount of oxygenated hemoglobin (oxyHb) was measured at 59%.

Thus oxygen was effectively and rapidly transferred from the gas core of the microbubbles to hemoglobin following a single inversion of the test tube. While much less oxygen was transferred into the blood by administering oxygen gas along. Light microscopy showed no evidence of gross hemolysis.

Example 4

Oxygen Release Kinetics Studies (In Vitro)

Microbubble Formation

For this study, microbubbles containing DPPC as the base lipid and PEG stearate as the emulsifying agent in a molar ration of 95:5 (base lipid:emulsifying agent), which were prepared according to the method of Example 1 without the concentration and size isolation steps. Following sonication, the microbubbles were removed by a pump and co-infused, without further processing or concentration steps, with venous human blood at varying rates. The microbubbles produced in this manner had a concentration of only 2-5 mL of oxygen per 50 mL of suspension.

The following rates were tested: 1 ml suspension/min, 2 ml suspension/min, 4 ml suspension/min and 5 ml suspension/min.

Analysis Methods

The oxygen release kinetics of the microbtibbles were tested for a dose-response relationship. Desaturated, whole blood was withdrawn from healthy volunteers and co-infused with the oxygenated microbubbles into a glass circuit designed to emulate convective blood flow. Temperature was maintained at 36° C. Blood was infused at 10 mL/minute.

Oxygen tension was measured five times at each rate, and the increase in $PO_2$ above baseline was plotted against infusion rate. Blood pH was also measured. $PCO_2$ (mm Hg) and serum bicarbonate concentrations (mmol/L) for the blood samples were also measured.

There was no macro- or microscopic evidence of frothing, clotting or hemolysis. There was no evidence of microbubbles by optical sizing or light microscopy in post-infusion samples.

Results

Figure 6:
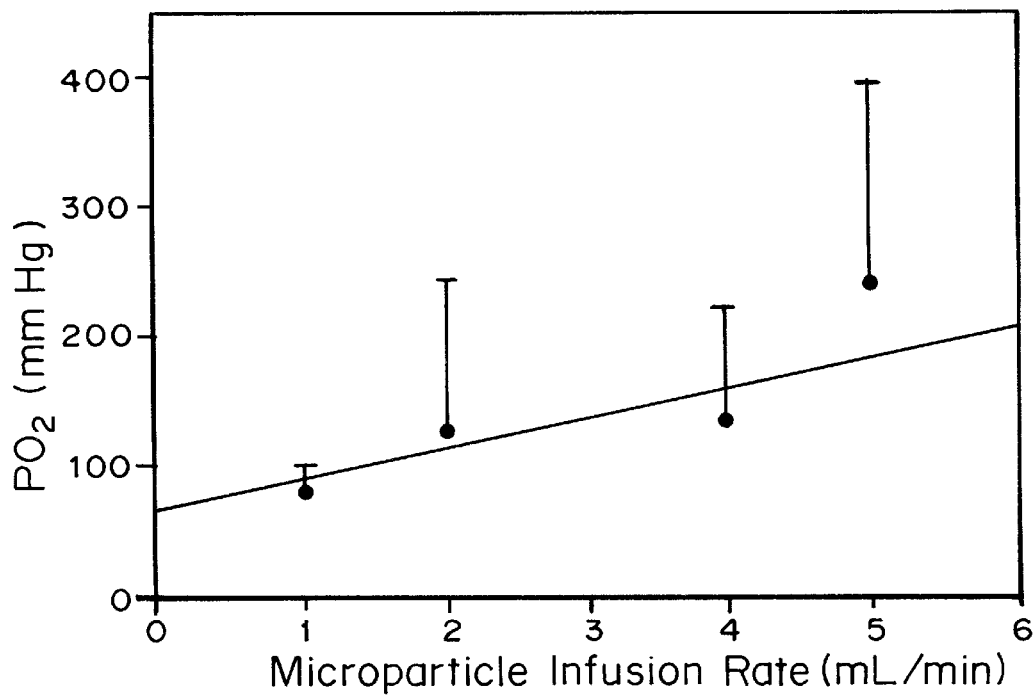
FIG. 6 is a graph of $PO_2$ (mmHg) versus microbubble infusion rate (mL/min) for infusions of DPPC (C16) oxygenated microbubbles (20 volume % (ml oxygen per dL suspension), mixed in normal saline) in human venous blood.
Figure 7:
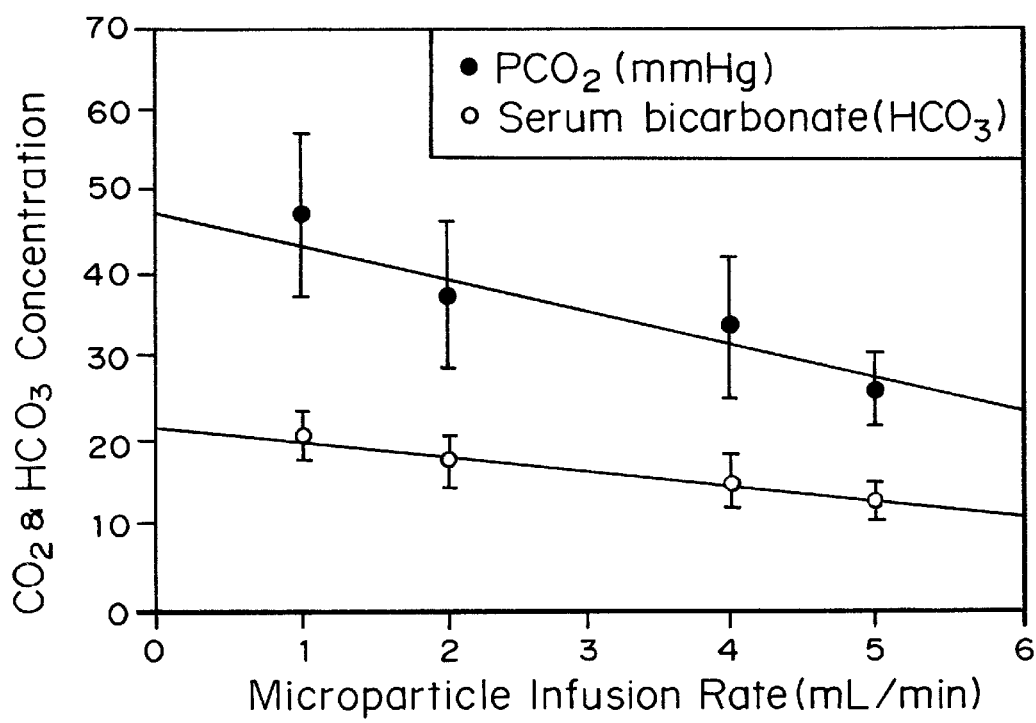
FIG. 7 is a graph of $PCO_2$ (mm Hg) (top line) and serum bicarbonate concentration measurements (mmol/L) (bottom line) versus microbubble infusion rate (mL/min) for infusions of DPPC (C16) oxygenated microbubbles (20 volume % (ml oxygen per dL suspension), mixed in normal saline) in human venous blood.

FIG. 6 shows results of the $PO_2$ measurements with DPPC (C16) and PEG stearate oxygenated microbubbles (20 volume % (ml oxygen per dL suspension), mixed in normal saline). FIG. 7 shows the results of the $PCO_2$ (mm Hg) and serum bicarbonate concentration (mmol·L) measurements for the microbubbles.

Microbubbles formed with C16 as the base lipid increased $PO_2$ by 50 mm Hg to greater than 500 mm Hg (depending upon infusion rate). As shown in FIG. 7, serum bicarbonate levels decreased with decreasing $PCO_2$ measurements, which decreased as the microbubble infusion rate increased.

Blood pH remained stable over time for each infusion rate. Blood pH ranges from about 7.25 to 7.30 for all of the experiments. This is due to the buffering capabilities of serum bicarbonate, which was noted to decrease with decreasing amounts of carbon dioxide (see FIG. 7).

This may be due to the unique behavior of hemoglobin as described by the hemoglobin dissociation curve. In the presence of high oxygen tension, hemoglobin preferentially sheds carbon dioxide and binds to oxygen. 'Shed' carbon dioxide dissolves into plasma (therefore, is not hemoglobin-bound and $PCO_2$ decreases) and is converted to carbonic acid (in turn buffered by bicarbonate, which decreases with increasing dissolved $CO_2$). Within the physiologic limits allowed by serum bicarbonate and other buffers, this allows for transfer of oxygen to erythrocytes in the bloodstream and the release of carbon dioxide without the development of acidosis

Example 5

Effect of Microbubble Size on Dissolution Time (In Vitro)

The effect of microbubble radius as an independent predictor of microparticle lifetime in a degassed aqueous environment was estimated by numerical simulation as follows. The partial pressures of the gases in the aqueous environment were held constant at $P_{O2}$ of 18 mmHg, $P_{CO2}$ of 45 mmHg, and $P_{N2}$ of 592.8 mmHg.

To model the gas release kinetics, a mass balance was performed about the microbubble as gases were either entering or leaving the microbubble from the surroundings, depending on the difference in partial pressures between the interior and exterior phases. Gas flux was positive in the direction of decreasing partial pressure. The microbubble was initially pure oxygen. Diffusion in the liquid phase was modeled to take place over a thin film equal to the microbubble radius. This is equivalent to the Sherwood number for a purely dissolving sphere. At the surface, the microbubble partial pressure was given by Henry's Law using the pressure inside the microbubble, which was the sum of the hydrostatic and Laplace pressures. At the diffusion layer boundary, the partial pressure was assumed to be equal to the bulk phase partial pressure. Diffusion was modeled according to Fick's Law. A component balance was taken at each time step for each gas species and summed to provide the total pressure and volume of gas inside the microbubble. The dynamics of microbubble dissolution were thus determined by numerical simulation. The dissolution time was given by the time to reach a radius of zero.

Results

Figure 8:
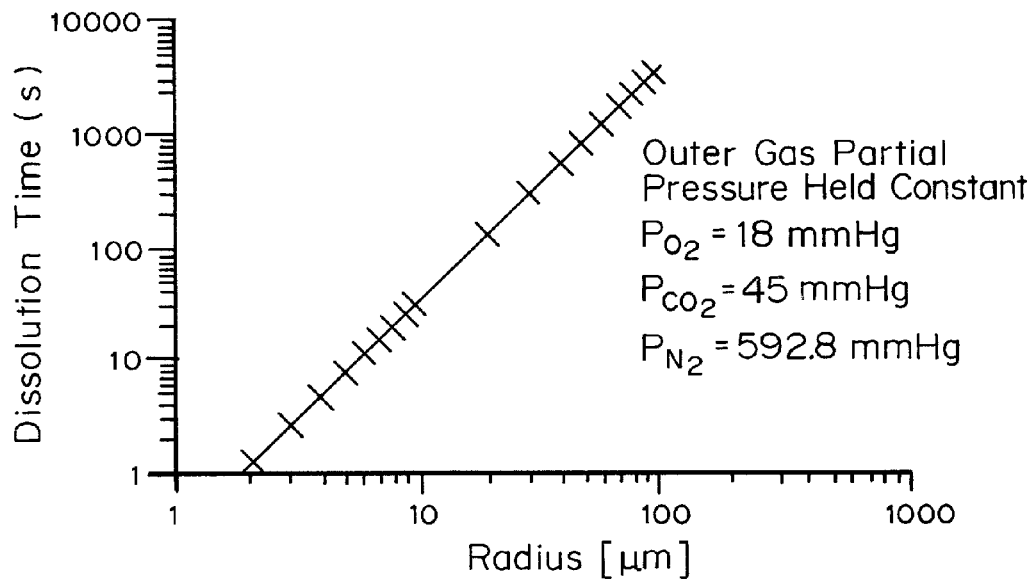
FIG. 8 is a graph of dissolution time (s) versus radius (μm) for a single microbubble encapsulating oxygen in a degassed aqueous environment.

Dissolution time was estimated to increase exponentially with increasing microbubble radius (FIG. 8). For microbubbles with a radius of about 2 μm, the gas was determined to be released and the bubble was determined to dissolve in less than 2 seconds in the aqueous environment. While for microbubbles with a radius of about 150 mm, it was determined to take about 5,000 seconds for the microbubble to dissolve. Based on these estimates, the preferred microbubble diameter appears to be 10-12 microns or less. This size range is estimated to provide a dissolution time of about 10 seconds or less.

Example 6

Particle Stability Testing

In some applications, it is helpful to provide stable microbubbles that can be stored for weeks or months following production. This study was directed at determining the longevity of stable microbubble suspensions.

60 mL syringes (Becton-Dickenson) were filled with 80 mL oxygen/dL microbubble suspension. The microbubble suspensions were formed as described in Example 1 and contained 95:5 molar C16 to 14:0 PE-PEG. Syringes were capped with a standard air-tight cap, and were stored at room temperature or 4° C., as noted.

Gas fraction was measured by the change in weight of the syringe divided by the volume of suspension within it. Prior to each measurement, large microbubbles were removed by mechanically agitating the sample, bringing the larger (more buoyant) microbubbles to the top of the syringe, allowing for expulsion from the syringe.

Particle sizing at each of the measurement points revealed no changes in particle size distribution following removal of buoyant microbubbles.

Figure 9:
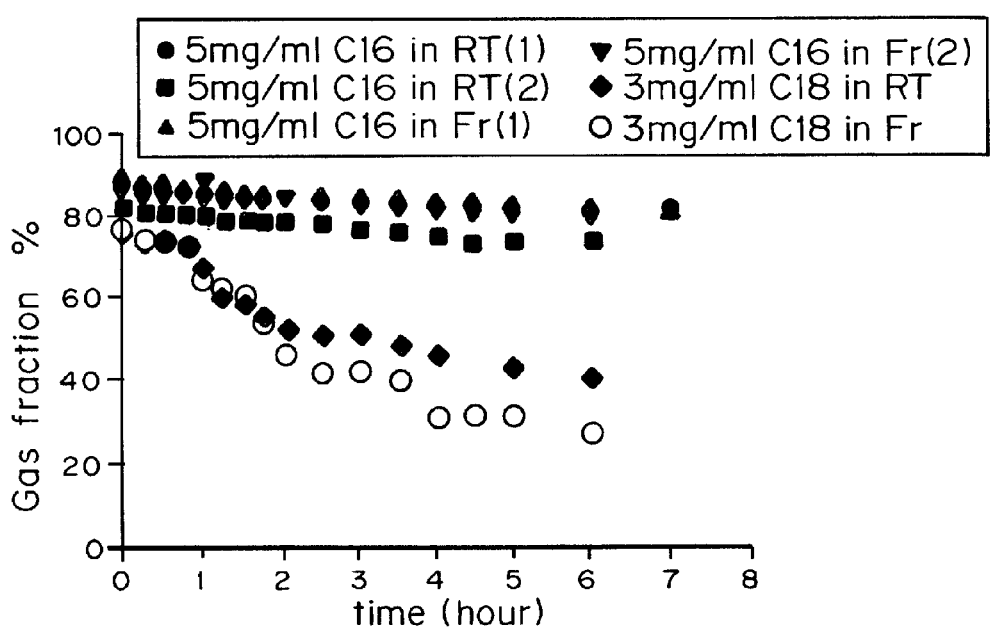
FIG. 9 is a graph of gas fraction % (mL of oxygen gas per dL of suspension) versus time (hours), where time 0 denotes the time of microbubble suspension creation.

As shown in FIG. 9, microbubbles composed of DPPC (C16) as the base lipid can be stored at room temperature and are preserved at 80 mL oxygen per dL suspension for at least 8 hours.

Microbubbles composed of C18 exhibit significant volume loss using the creation and storage techniques used in this study.

Example 7

In Vivo Tests

The following experimental results provide data from two in vivo experiments. To test the ability of microparticles to diffuse oxygen into ischemic tissues and desaturated blood, test were conducted in a rabbit model of hypoxemic ventilation. All animal experiments were approved by the Institutional Animal Care and Use Committee of Children's Hospital Boston. Animals were housed and surgical procedures took place under the supervision of a staff veterinarian in the Animal Research facility of Children's Hospital Boston (ARCH).

Animal Preparation: Two male New Zealand rabbits (3-4 kg) were purchased (Milbrook Farms, Milbrook, Mass.) and were allowed a three day acclimation period. Animals received appropriate intravenous analgesia and sedation, endotracheal intubation, and surgical placement of central venous catheters (PESO catheters) into the right internal jugular vein, femoral vein and femoral artery. Animals were allowed to breathe room air spontaneously until the start of the experimental procedure. Sedation and analgesia were maintained by continuous infusions of Fentanyl and Midazolam.

Microbubble Preparation: The microbubbles utilized for this study were composed of 1,2-Dipalmitoyl-sn-Glycero-3-Phosphocholine (C16) mixed in a 95:5 molar ratio with 14:0 PE-PEG (550), as described in Example 1. 200 mL of microbubbles were formed within 1 hour. The resultant suspension exhibited a concentration of 80 mL oxygen/dL suspension, and particle sizing via microscopy revealed that the microbubbles had diameters of less than 15 microns.

Experimental Procedure: Animals were ventilated using 15% oxygen, 85% nitrogen. Animals were provided a mandatory respiratory rate to ensure adequate minute ventilation. End-tidal carbon dioxide and end-tidal oxygen content, pulse oximetry, blood pressure and EKG were monitored continuously. In the animals tested (n=2), the animals became pulseless just following the induction of acute hypoxemia. The thorax and pericardium were opened to observe the heart under direct visualization. Ventilation was discontinued to maximize visualization. Microbubble suspensions were then injected via internal jugular catheter in 1 mL aliquots to provide rescue oxygenation.

Experimental Results: Upon opening the thorax, rabbit hearts were found to be cyanotic, dyskinetic and severely bradycardic (heart rate of about 10 beats/minute), following loss of pulsatility. Microbubble suspensions were then injected into the internal jugular catheter, and were seen entering the right atrium (microbubble suspensions are white and were easily visualized in the bloodstream). There was no other drug mixed with the microbubble suspension.

Immediately upon entering the atrium, atrial contractions increased significantly in force and frequency. Seconds later, right ventricular function and rate improved (heart rate of about 100 beats/minute). Microbubbles were subsequently noted in the left atrium, with subsequent improved left atrial and ventricular function after about 2 minutes following injection.

In both animals, the heart was perfused with aliquots of microbubble suspensions. The lungs remained collapsed throughout the duration of the experiment.

In the first animal, ventricular function was maintained for 90 minutes in this manner.

In the second animal, in the process of exposing the thorax, the superior vena cava was unintentionally lacerated. A hemorrhage of approximately 20 mL/kg in the setting of severe bradycardia occurred. The microbubble infusion was injected into the internal jugular venous catheter. As in the first animal experiment, microbubbles were also visualized entering the right atrium. Atrial and ventricular function were noted to improve in chronotropy and inotropy following microbubble contact with the myocardium.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method for delivering oxygen to a patient, comprising administering via injection or infusion to the patient a composition, comprising a suspension comprising microbubbles and a carrier, wherein the microbubbles comprise a lipid envelope and a gas core, wherein the gas core comprises oxygen and does not contain a fluorinated gas, wherein the lipid envelope comprises one or more lipids, wherein the lipid is a phospholipid comprising acyl chains having an average length of 10 to 24 carbons, wherein the outer surface of the lipid envelope forms a protective border, and wherein the suspension comprises at least 40% oxygen by volume,
wherein the patient is experiencing local or systemic hypoxia,
wherein the composition is administered in an effective amount to increase the concentration of oxygen in the patient's blood, tissue or organ in need of oxygen, and
wherein the microbubbles release the effective amount of oxygen within 0.5 seconds to 1 minute following administration to the patient.

2. The method of claim 1, wherein the lipid envelope is a monolayer.

3. The method of claim 1, wherein the oxygen is administered via injection.

4. The method of claim 1, wherein the hypoxic conditions arise in the patient as a result of a disease or disorder selected from the group consisting of congenital physical or physiologic diseases or disorders, embolisms, peripheral artery occlusive disease, transient ischemic attacks, strokes, acute trauma, surgical interventions, and exposure to chemical or environmental agents.

5. The method of claim 1, wherein the suspension comprises 40 to 70% oxygen by volume.

6. The methods of claim 1, wherein the composition is administered at a rate of 0.5 to 400 mL/minute.

7. A method for delivering oxygen to a patient, comprising administering via injection or infusion to the patient a composition, comprising a suspension comprising microbubbles and a carrier, wherein the microbubbles comprise a lipid envelope and a gas core, wherein the gas core comprises oxygen and does not contain a fluorinated gas, wherein the lipid envelope comprises one or more lipids, wherein the lipid is a saturated diacyl phosphatidylcholine having the formula Di-$C_n$-PC, where n is between 12 and 24, wherein the outer surface of the lipid envelope forms a protective border, and wherein the suspension comprises at least 40% oxygen by volume,
wherein the patient is experiencing local or systemic hypoxia,
wherein the composition is administered in an effective amount to increase the concentration of oxygen in the patient's blood, tissue or organ in need of oxygen, and
wherein the microbubbles release the effective amount of oxygen within 0.5 seconds to 1 minute following administration to the patient.

8. The method of claim 7, wherein the lipid is a saturated diacyl phosphatidylcholine having the formula Di-$C_n$-PC, where n is 16 or 18.

9. The method of claim 1, wherein the microbubbles are stable at 4° C. and standard pressures for weeks to months.

10. The method of claim 7, wherein the lipid envelope further comprises a sterol.

11. The method of claim 1, wherein the amount of oxygen that is released is effective to raise the oxygen content of circulating blood.

12. The method of claim 11, wherein the amount of oxygen that is released is effective to restore $PO_2$ levels to normal levels.

13. The method of claim 11, wherein the amount of oxygen that is released is effective to resuscitate the patient's heart.

14. The method of claim 1, wherein the oxygen is administered as a continuous infusion.

* * * * *